(12) United States Patent
Sengupta et al.

(10) Patent No.: US 8,188,022 B2
(45) Date of Patent: May 29, 2012

(54) MULTILAYER FRAGRANCE ENCAPSULATION COMPRISING KAPPA CARRAGEENAN

(75) Inventors: Tapashi Sengupta, Barrington, IL (US); Ashoke K. SenGupta, Barrington, IL (US)

(73) Assignee: AMCOL International Corporation, Hoffman Estates, IL (US)

( * ) Notice: Subject to any disclaimer, the term of this patent is extended or adjusted under 35 U.S.C. 154(b) by 529 days.

(21) Appl. No.: 12/422,791

(22) Filed: Apr. 13, 2009

(65) Prior Publication Data

US 2009/0258812 A1      Oct. 15, 2009

Related U.S. Application Data

(63) Continuation-in-part of application No. 12/397,043, filed on Mar. 3, 2009, now Pat. No. 7,977,288, and a continuation-in-part of application No. 12/327,570, filed on Dec. 3, 2008, now Pat. No. 7,871,972.

(60) Provisional application No. 61/044,384, filed on Apr. 11, 2008, provisional application No. 61/044,381, filed on Apr. 11, 2008, provisional application No. 61/101,336, filed on Sep. 30, 2008.

(51) Int. Cl.
*C11D 3/50* (2006.01)

(52) U.S. Cl. ......... 510/101; 510/438; 510/441; 510/519

(58) Field of Classification Search ................... 510/101, 510/438, 441, 519
See application file for complete search history.

(56) References Cited

U.S. PATENT DOCUMENTS

| | | | |
|---|---|---|---|
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,723,325 A | 3/1973 | Parran |
| 3,870,542 A | 3/1975 | Ida et al. |
| 4,145,184 A | 3/1979 | Brain et al. |
| 4,152,272 A | 5/1979 | Young |
| 4,318,818 A | 3/1982 | Letton et al. |
| 4,387,090 A | 6/1983 | Bolich, Jr. |
| 4,402,856 A | 9/1983 | Schnoring et al. |
| 4,424,134 A | 1/1984 | Sissin et al. |
| 4,446,032 A | 5/1984 | Munteanu et al. |
| 4,446,042 A | 5/1984 | Leslie |
| 4,464,271 A | 8/1984 | Munteanu et al. |
| 4,515,705 A | 5/1985 | Moeddel |
| 4,534,891 A | 8/1985 | Boden et al. |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,664,064 A | 5/1987 | Lowe |
| 4,673,568 A | 6/1987 | Grollier et al. |
| 4,690,825 A | 9/1987 | Won |
| 4,705,681 A | 11/1987 | Maes et al. |
| 4,710,374 A | 12/1987 | Grollier et al. |
| 4,714,562 A | 12/1987 | Roselle et al. |
| 4,767,547 A | 8/1988 | Straathof et al. |
| 4,842,849 A | 6/1989 | Grollier et al. |
| 4,946,624 A | 8/1990 | Michael |
| 4,948,818 A | 8/1990 | Carmody et al. |
| 4,954,285 A | 9/1990 | Wierenga et al. |
| 4,962,133 A | 10/1990 | Chromecek et al. |
| 4,962,170 A | 10/1990 | Chromecek et al. |
| RE33,429 E | 11/1990 | Abrutyn |
| 4,968,451 A | 11/1990 | Scheibel et al. |
| 4,973,422 A * | 11/1990 | Schmidt .................... 510/337 |
| 5,085,857 A | 2/1992 | Reid et al. |
| 5,112,688 A | 5/1992 | Michael |
| 5,126,061 A | 6/1992 | Michael |
| 5,137,646 A | 8/1992 | Schmidt et al. |
| 5,145,842 A | 9/1992 | Driedger et al. |
| 5,169,552 A | 12/1992 | Wise |
| 5,194,639 A | 3/1993 | Connor et al. |
| 5,207,998 A | 5/1993 | Robinson et al. |
| 5,275,755 A | 1/1994 | Sebag et al. |
| 5,288,417 A | 2/1994 | Bauer et al. |
| 5,288,431 A | 2/1994 | Huber et al. |
| 5,306,434 A | 4/1994 | Schueller et al. |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |

(Continued)

FOREIGN PATENT DOCUMENTS

EP      0397246 A2      11/1990

(Continued)

OTHER PUBLICATIONS

International Search Report for International application No. PCT/US2006/001019 (Jun. 7, 2006) by the European Patent Office (2 pages).
Poucher W.A. Perfumes Cosmetics and Soaps. Second Edition. 1959.
Internatinoal Preliminary Report of Patentability for International Application No. PCT/US2006/001019 (Jul. 17, 2007) by the International Bureau of WIPO (7 pages).
International Search Report for International Application No. PCT/US2008/006138 (Oct. 31, 2008) by The Korean Intellectual Propery Office (2 pages).
International Search Report and Written Opinion for International Application No. PCT/US2009/040376, dated Nov. 20, 2009.

(Continued)

*Primary Examiner* — Charles Boyer
(74) *Attorney, Agent, or Firm* — Marshall, Gerstein & Borun LLP

(57) ABSTRACT

Disclosed herein is a fragrance composition and a method for making the same having a fragrance particulate and a viscoelastic gel; where the composition has enhanced fragrance retention throughout the processing of the composition.

6 Claims, 13 Drawing Sheets

U.S. PATENT DOCUMENTS

| | | |
|---|---|---|
| 5,500,152 A | 3/1996 | Helliwell |
| 5,543,074 A | 8/1996 | Hague et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins et al. |
| 5,618,523 A | 4/1997 | Zysman et al. |
| 5,661,118 A | 8/1997 | Cauwet et al. |
| 5,674,832 A | 10/1997 | Keys |
| 5,677,407 A | 10/1997 | Sojka |
| 5,679,630 A | 10/1997 | Baeck et al. |
| 5,703,030 A | 12/1997 | Perkins et al. |
| 5,703,034 A | 12/1997 | Offshack et al. |
| 5,705,464 A | 1/1998 | Scheper et al. |
| 5,712,358 A | 1/1998 | Sojka |
| 5,726,138 A | 3/1998 | Tsaur et al. |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,777,054 A | 7/1998 | Sojka |
| 5,830,960 A | 11/1998 | Sojka |
| 5,830,967 A | 11/1998 | Sojka |
| 5,834,577 A | 11/1998 | Sojka |
| 5,837,661 A | 11/1998 | Evans et al. |
| 5,837,790 A | 11/1998 | Sojka |
| 5,853,707 A | 12/1998 | Wells et al. |
| 5,877,145 A | 3/1999 | Wahl et al. |
| 5,902,781 A | 5/1999 | Painter |
| 5,914,101 A | 6/1999 | Tapley et al. |
| 5,914,307 A | 6/1999 | DeNome et al. |
| 5,916,862 A | 6/1999 | Morelli et al. |
| 5,923,203 A | 7/1999 | Chen et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,955,552 A | 9/1999 | Sojka |
| 5,962,386 A | 10/1999 | Scheper et al. |
| 5,968,286 A | 10/1999 | Crudele et al. |
| 5,968,881 A | 10/1999 | Haeggberg et al. |
| 5,990,059 A | 11/1999 | Finel et al. |
| 5,990,065 A | 11/1999 | Vinson et al. |
| 6,017,871 A | 1/2000 | Baeck et al. |
| 6,020,294 A | 2/2000 | Getty et al. |
| 6,024,943 A | 2/2000 | Ness et al. |
| 6,051,540 A | 4/2000 | Shefer et al. |
| 6,069,122 A | 5/2000 | Vinson et al. |
| 6,080,708 A | 6/2000 | Glenn, Jr. et al. |
| 6,107,429 A | 8/2000 | Sojka |
| 6,126,954 A | 10/2000 | Tsaur |
| 6,156,713 A | 12/2000 | Chopra et al. |
| 6,162,423 A | 12/2000 | Sebag et al. |
| 6,248,849 B1 | 6/2001 | Sojka |
| 6,261,483 B1 | 7/2001 | Frank et al. |
| 6,277,361 B1 | 8/2001 | Murray et al. |
| 6,329,057 B1 | 12/2001 | Dungworth et al. |
| 6,335,315 B1 | 1/2002 | Trinh et al. |
| 6,387,995 B1 | 5/2002 | Sojka |
| 6,436,383 B2 | 8/2002 | Murray et al. |
| 6,541,565 B2 | 4/2003 | Hood et al. |
| 6,667,029 B2 | 12/2003 | Zhong et al. |
| 6,706,258 B1 | 3/2004 | Gallagher et al. |
| 6,740,631 B2 | 5/2004 | Shefer et al. |
| 6,790,814 B1 | 9/2004 | Marin et al. |
| 6,844,302 B1 | 1/2005 | Boden et al. |
| 6,869,923 B1* | 3/2005 | Cunningham et al. ........... 512/4 |
| 7,118,057 B2 | 10/2006 | Hao et al. |
| 7,119,057 B2 | 10/2006 | Popplewell et al. |
| 7,119,060 B2 | 10/2006 | Shefer et al. |
| 7,122,512 B2 | 10/2006 | Brain et al. |
| 7,125,835 B2 | 10/2006 | Bennett et al. |
| 7,196,049 B2 | 3/2007 | Brain et al. |
| 7,294,612 B2* | 11/2007 | Popplewell et al. .............. 512/4 |
| 2003/0049282 A1 | 3/2003 | Aronson et al. |
| 2003/0180340 A1* | 9/2003 | Birch et al. .................. 424/401 |
| 2003/0224954 A1 | 12/2003 | Wells et al. |
| 2003/0228339 A1 | 12/2003 | El-Nokaly et al. |
| 2004/0214742 A1* | 10/2004 | Meli et al. ..................... 510/504 |
| 2005/0158266 A1 | 7/2005 | Peffly et al. |
| 2005/0202992 A1* | 9/2005 | Portabales et al. ........... 510/446 |
| 2005/0227907 A1 | 10/2005 | Lee |
| 2005/0244356 A1 | 11/2005 | Aronson et al. |
| 2006/0014655 A1 | 1/2006 | Smets |
| 2006/0052272 A1* | 3/2006 | Meli et al. ..................... 510/504 |
| 2006/0128586 A1* | 6/2006 | Lant et al. ..................... 510/392 |
| 2006/0177273 A1 | 8/2006 | Bonnemaire et al. |
| 2006/0248665 A1* | 11/2006 | Pluyter et al. ..................... 8/406 |
| 2007/0104659 A1* | 5/2007 | Yasuda et al. .................... 424/49 |
| 2007/0111919 A1* | 5/2007 | Boerefijn et al. ............. 510/445 |
| 2008/0090586 A1 | 4/2008 | Engelhart |
| 2008/0146478 A1* | 6/2008 | Lei et al. ....................... 510/119 |
| 2009/0258042 A1* | 10/2009 | Anastasiou et al. .......... 424/401 |

FOREIGN PATENT DOCUMENTS

| | | |
|---|---|---|
| EP | 1160311 A2 | 12/2001 |
| FR | 2774389 A1 | 8/1999 |
| WO | WO-9811869 | 3/1998 |
| WO | WO-9811870 | 3/1998 |
| WO | WO-00/46337 A1 | 8/2000 |
| WO | WO-0174310 A2 | 10/2001 |
| WO | WO-02/09663 A1 | 2/2002 |
| WO | WO-2006/076454 A | 7/2006 |
| WO | WO-2008/127766 A2 | 10/2008 |
| WO | WO-2008/145547 A1 | 12/2008 |

* cited by examiner

MULTILAYER FRAGRANCE ENCAPSULATION COMPRISING KAPPA CARRAGEENAN

CROSS-REFERENCE TO RELATED APPLICATIONS

This application claims the benefit of priority of Provisional Patent Application Nos. 61/044,384, filed Apr. 11, 2008, 61/044,381, filed Apr. 11, 2008, and 61/101,336, filed Sep. 30, 2008; is a continuation-in-part of U.S. patent application Ser. No. 12/397,043, filed Mar. 3, 2009; and is a continuation-in-part of U.S. patent application Ser. No. 12/327,570, filed Dec. 3, 2008; each incorporated herein by reference in their entirety.

BACKGROUND OF THE INVENTION

1. Field of the Disclosure

The disclosure generally relates to a fragrance-releasing composition including a fragrance particulate coated with one or more layers of a viscoelastic gel for enhanced fragrance retention and methods of manufacturing and using the fragrance-releasing composition.

2. Brief Description of Related Technology and Prior Art

The consumer products industry has long searched for ways to enhance the fragrance performance of products such as liquid soap, bodywash, laundry detergents, dishwashing detergents, shampoos, conditioners, surface cleaners, and particularly for fabric care products, like a fabric softener, and to make the products more esthetically pleasing to consumers. For example, fragrance is an important ingredient in successful commercial fabric care products because, in addition to imparting an esthetically pleasing odor, a fragrance conveys a positive image of product performance to the consumer, e.g., the fabric is clean and fresh.

Fragrances typically are added to fabric care products to provide a fresh, clean impression for the product itself, as well as to the fabric treated with the product. Although the fragrance does not enhance the performance of a fabric care product, the fragrance makes these products more esthetically pleasing, and consumers expect and demand a pleasing odor for such products.

A fragrance plays an important, and often a determining, role when the consumer selects and purchases a fabric care product. Many consumers desire the fragrance to be deposited on the fabric and remain on the fabric for an extended time in order to convey a continuing impression of freshness. Consumers also desire fabric care products that impart a sufficient fragrance level to the fabric, and, in some embodiments, release the fragrance when the fabric is ironed.

Introduction of a fragrance into or onto a substrate, such as via a fabric care product, is restricted by considerations such as availability and cost, and also by an inability of the fragrance to sufficiently deposit onto the substrate, and then remain on the substrate for an extended period of time. Fabric care products, particularly, should remain on the fabric during the wash, rinse, and drying cycles. For example, a substantial amount of the fragrance deposited on a fabric is removed from the fabric during the drying process, even when the treated fabrics are line dried. It also has been demonstrated that a substantial amount of the fragrance in currently available fabric care products is lost during wash/rinse cycles. This fragrance loss is attributed to the water solubility of various fragrance ingredients, to the volatility of fragrance ingredients that deposit on the fabric, and the wash-off of the fragrance from the fabric.

Typical fabric care products, such as laundry detergent compositions and fabric softener compositions, contain about 0.1% to about 1.5%, by weight, of a fragrance. U.S. Pat. No. 6,051,540 discloses that in the course of the washing clothes with a standard powdered laundry detergent, or a fabric softener rinse, only a small fraction of the fragrance present in these fabric care products is actually transferred to the fabric, i.e., as low as 1% of the original amount of fragrance present in these products.

Attempts have been made to increase fragrance deposition onto fabric, and to hinder or delay the release of the fragrance from the fabric, such that the laundered fabric remains esthetically pleasing for an extended length of time. One approach uses a carrier to introduce the fragrance to the fabric. The carrier is formulated to contain a fragrance and to adhere to the fabric during a washing cycle through particle entrainment or chemical change.

Fragrances have been adsorbed onto various materials, such as silica and clay, for delivery of the fragrance from detergents and fabric softeners to fabrics. U.S. Pat. No. 4,954,285 discloses fragrance particles especially for use with dryer-released fabric softening/antistatic agents. The fragrance particles are formed by adsorbing the fragrance onto silica particles having a diameter of greater than about one micron. The fragrance particles are included in dryer-activated solid fabric softener compositions containing coated particles of fabric softener. The compositions release softener to fabrics in the dryer, and the fragrance particles improve the esthetic character of the fabric softener deposited on the fabric. The fragrance particles also can be admixed with detergent granules and can be coated or uncoated. This system has a drawback in that the fragrance is not sufficiently protected, and frequently is lost or destabilized during processing.

Another problem often associated with perfumed fabric care products is excessive odor intensity. A need therefore exists for a fragrance delivery product that provides satisfactory fragrance both during use and from the dry laundered fabric, and also provides prolonged storage benefits and an acceptable odor intensity of the fabric care product.

U.S. Pat. No. 6,790,814 discloses that a fragrance loaded into a porous carrier (material), such as zeolite particles, can be effectively protected from premature release of the fragrance by coating the loaded carrier particles with a hydrophobic oil, then encapsulating the resulting carrier particles with a water-soluble or water-dispersible, but oil-insoluble, material, such as a starch or modified starch.

U.S. Pat. Nos. 4,946,624; 5,112,688; and 5,126,061 disclose microcapsules prepared by a coacervation process. The microcapsules have a complex structure, with a large central core of encapsulated material, preferably a fragrance, and walls that contain small wall inclusion particles of either the core material or another material that can be activated to disrupt the wall for release of fragrance. The microcapsules are incorporated into a fabric softener composition having a pH of about 7 or less and which further contains a cationic fabric softener. The encapsulated fragrance preferably is free of large amounts of water-soluble ingredients. The microcapsules are added separately to the fabric softener compositions. Ingredients that have high and low volatilities, compared to the volatility of a desired fragrance, either can be added to or removed from the fragrance to achieve the desired volatility. This type of controlled release system cannot be used with all types of fragrance ingredients, in particular, with fragrance ingredients that are relatively water soluble and/or are incapable of depositing onto a fabric.

U.S. Pat. No. 4,402,856 discloses a coacervation technique to provide fragrance particles for fabric care products containing gelatin or a mixture of gelatin with gum arabic, carboxymethylcellulose, and/or anionic polymers. The gelatin is hardened with a natural and/or synthetic tanning agent and a carbonyl compound. The particles adhere to the fabric during rinse cycles, and are carried over to the dryer. Diffusion of the fragrance from the capsules occurs only in the heat-elevated conditions of a dryer.

U.S. Pat. No. 4,152,272 discloses incorporating a fragrance into wax particles to protect the fragrance during storage and through the laundry process. The fragrance/wax particles are incorporated into an aqueous fabric conditioner composition. The fragrance diffuses from the particles onto the fabric in the heat-elevated conditions of the dryer.

U.S. Pat. Nos. 4,446,032 and 4,464,271 disclose liquid or solid fabric softener compositions comprising microencapsulated fragrance suspensions. The compositions contain sustained release fragrances prepared by combining nonconfined fragrance oils with encapsulated or physically entrapped fragrance oils. These combinations are designed such that the nonconfined fragrance oil is bound in a network of physically entrapped fragrance oil and suspending agent. The controlled release system comprises a mixture of (i) a nonconfined fragrance composition, (ii) one or more fragrance oils which are physically entrapped in one or more types of solid particles, and (iii) a suspending agent such as hydroxypropyl cellulose, silica, xanthan gum, ethyl cellulose, or combinations thereof. The nonconfined fragrance, the entrapped fragrance, and the suspending agent are premixed prior to preparation of the liquid or solid fabric softener compositions.

U.S. Pat. Nos. 4,973,422 and 5,137,646 disclose fragrance particles for use in cleaning and conditioning compositions. The particles comprise a fragrance dispersed within a wax material. The particles further can be coated with a material that renders the particles more substantive to the surface being treated, for example, a fabric in a laundry process. Such materials help deliver the particles to the fabric and maximize fragrance release directly on the fabric. In general, the coating materials are water-insoluble cationic materials.

U.S. Pat. No. 6,024,943 discloses particles containing absorbed liquids and methods of making the particles. A fragrance is absorbed within organic polymer particles, which further have a polymer at their exterior. The external polymer has free hydroxyl groups, which promote deposition of the particles from a wash or rinse liquor. The external polymer can be a component of an encapsulating shell, but typically is used as a stabilizer during polymerization of the particles. A highly hydrolyzed polyvinyl alcohol is a preferred external polymer.

U.S. Pat. No. 6,740,631 discloses a free-flowing powder formed from solid hydrophobic, positively-charged nanospheres containing an active ingredient, such as a fragrance, encapsulated in a moisture sensitive microsphere. To maximize deposition of the nanospheres on a fabric, particle size is optimized to ensure entrainment of the particles within the fabric fibers, and a sufficiently high cationic charge density on the particle surface is provided to maximize an ionic attraction between the particles and the fabric.

U.S. Pat. No. 7,119,057 discloses a polymeric encapsulated fragrance where the fragrance encapsulating polymer is coated with one cationic polymer. The cationic polymer aids in the deposition and stability of the polymeric encapsulated fragrance. The load of the cationic polymer is preferably from about 10% to about 500% of the fragrance containing composition, based on a ratio with the fragrance on a dry basis.

U.S. Pat. No. 7,119,060 discloses solid spheres comprising a crystallized waxy material. The waxy material may have a fragrance or other active agent incorporated therein, together with a cationic, hydrophobic charge-enhancing agent and a cationic softening agent. The spheres adhere to a fabric because of the cationic charge, and when ironing a dried fabric, a burst of fragrance occurs. The load of fragrance or other active agent is limited to about 30%, by weight, of the waxy material.

U.S. patent application Ser. No. 11/231,082, filed Sep. 20, 2005 discloses the delivery of a benefit agent that is introduced into a formulation after admixture with a carrier. The agent and carrier composition requires a viscosity of at least 400 cps.

Generally, the prior art does not sufficiently teach or suggest a composition having a fragrance particulate coated with one or more layers of a viscoelastic gel for increased fragrance retention. Moreover, the prior art neither teaches nor suggests a methodology for making a fragrance particulate coated with one or more layers of a viscoelastic gel nor a method for the manufacture of a fragrance-releasing consumer products having enhanced fragrance retention imparted by viscoelastic gels.

SUMMARY OF THE INVENTION

The present disclosure relates to compositions comprising a viscoelastic gel and at least one fragrance. The compositions can further include carrier agents for the fragrance, coating agents for the fragrance, other benefit agents, deposition aids, and the like. The compositions described herein can be used in cleansing products, such as shampoos, conditioners, body washes, moisturizing agents, creams, shower gels, soaps, detergents, toothpastes, surface cleansing agents, and surface-conditioning agents, such as fabric softeners. The fragrance-releasing compositions described herein are not useful as a human food or for delivery to the mouth as a flavoring material.

In one embodiment, the fragrance in the form of a fragrance particulate is coated with a viscoelastic gel and the resulting coated fragrance composition is homogenized and dried. The dry fragrance composition is then applicable for use in admixing with other materials or compositions. Alternatively the dry coated fragrance composition can be further coated and/or entrapped within other materials and then used in admixing with other materials or compositions.

In another embodiment the fragrance composition is made by admixing the fragrance particulate with the viscoelastic gel. The fragrance particulate can be absorbed or adsorbed in or on carrier agents and/or be coated with a coating agent prior to admixing with a viscoelastic gel.

In yet another embodiment the fragrance composition may be further admixed with a deposition aid to facilitate and improve the adherence of the fragrance composition to a substrate.

In another embodiment of the compositions and methods described herein, it is an object to provide a more efficient method than the methods described in the prior art, for the deposition and retention of hydrophobic or oil-based benefit agents and fragrances from detersive cleansing and/or rinse-off compositions that do not adversely affect the stability, detergency, and foaming properties of the cleansing product compositions. A related object is to provide stable, low-cost, compositions that allow significantly high deposition and retention of hydrophobic benefit agents and/or fragrances onto substrates being treated with the compositions, including the fabric, hair, and skin.

Additional features of the invention may become apparent to those skilled in the art from a review of the following detailed description, taken in conjunction with the drawings, the examples, and the appended claims.

BRIEF DESCRIPTION OF THE DRAWINGS

For a more complete understanding of the disclosure, reference should be made to the following detailed description and accompanying drawings wherein.

Figure 1:
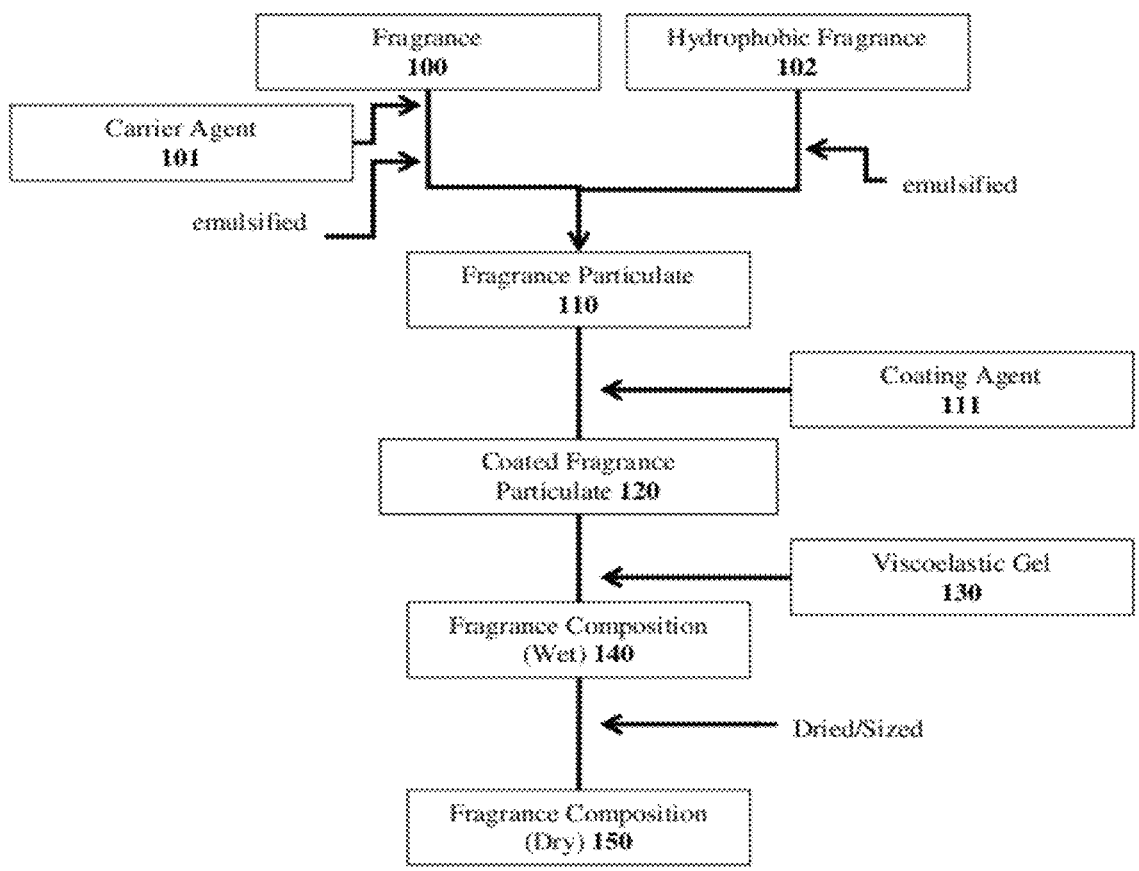
FIG. 1 is a schematic representation of some necessary and some optional steps, provided herein, for the production of a dry fragrance composition. The fragrance particulate 110 can be made by multiple methods; two methods are shown. First a fragrance 100 (hydrophobic or not) is admixed with a carrier agent 101 and the mixture is emulsified; alternatively, a hydrophobic fragrance 102 is emulsified. Shown here, the fragrance particulate 110 is optionally coated with a coating agent 111 yielding a coated fragrance particulate 120. The coated fragrance particulate 120 is then admixed with a viscoelastic gel 130 forming a wet fragrance composition 140. The wet fragrance composition can then be dried, ground, and sized to yield a dried fragrance compositions 150.
Figure 2:
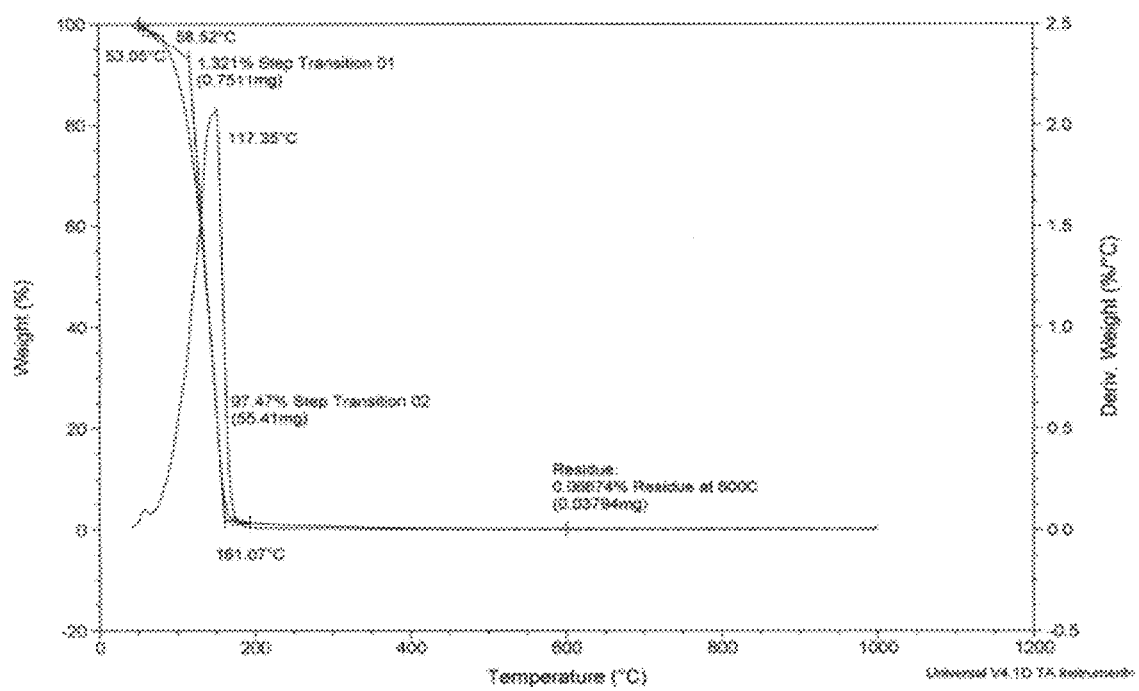
FIG. 2 is a plot of weight loss data for a sample of neat lavender fragrance from thermogravimetric analysis (TGA). The plot shows a single weight loss event with an onset of weight loss at about 58° C. and 100% weight loss by 161° C.
Figure 3:
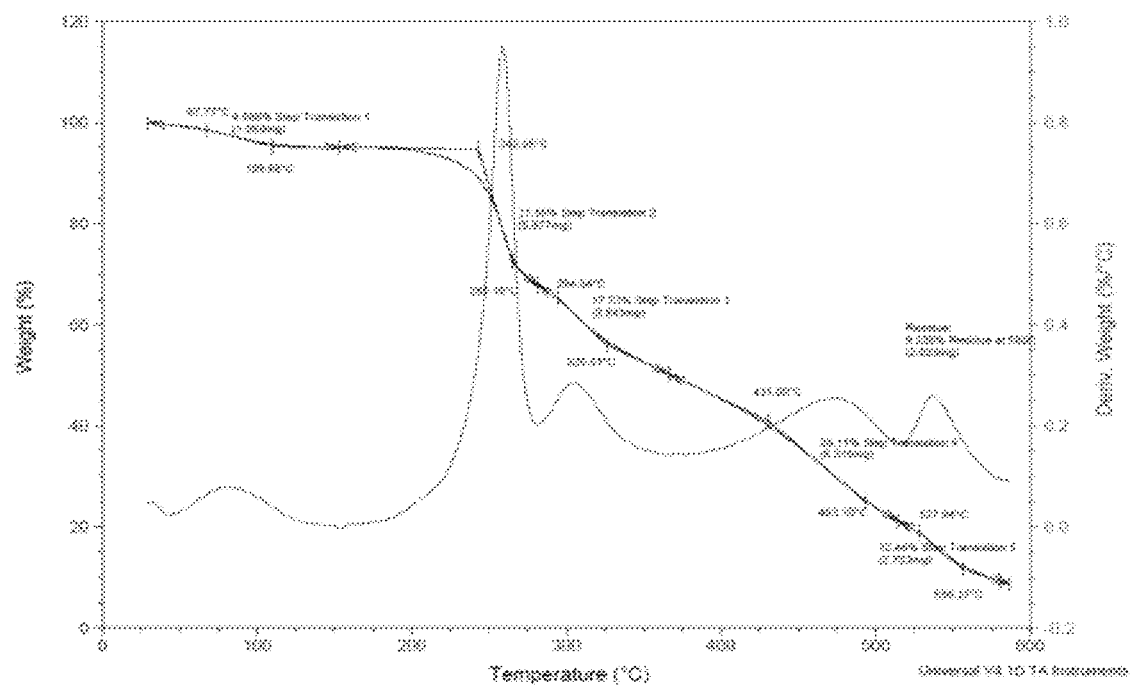
FIG. 3 is a plot of weight loss data for a sample of soy protein isolate from TGA. The plot shows water loss between 50° C. and 100° C. and four weight loss events above 225° C.
Figure 4:
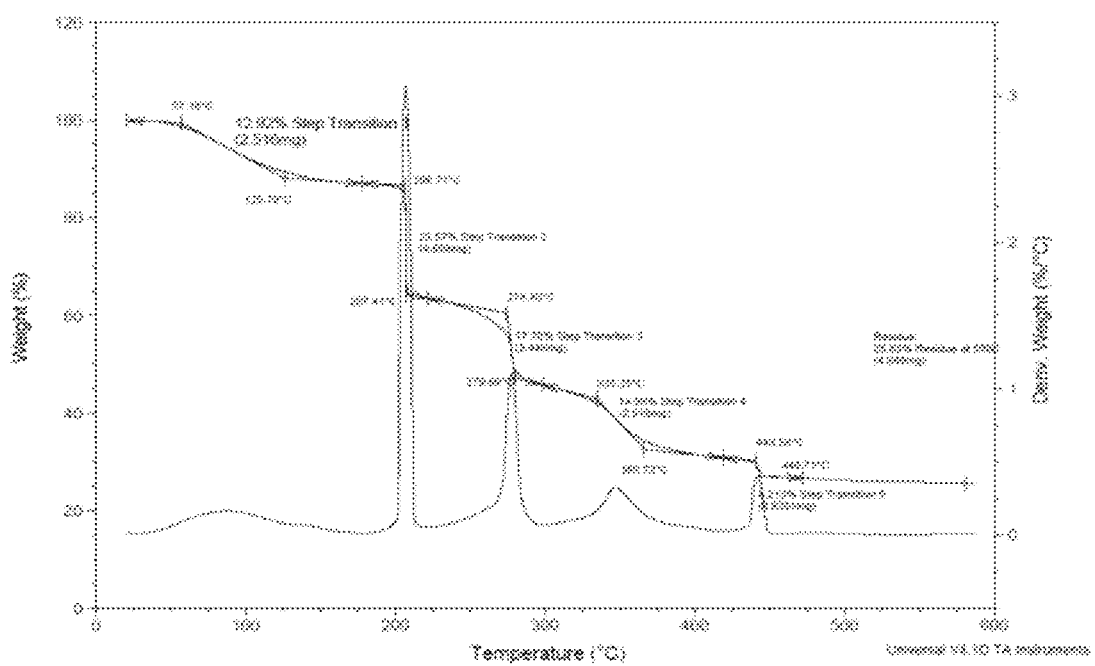
FIG. 4 is a plot of weight loss data for a sample of viscoelastic gel (Gelcarin) from TGA. The plot shows water loss between 60° C. and 125° C. and four weight loss events above 200° C.
Figure 5:
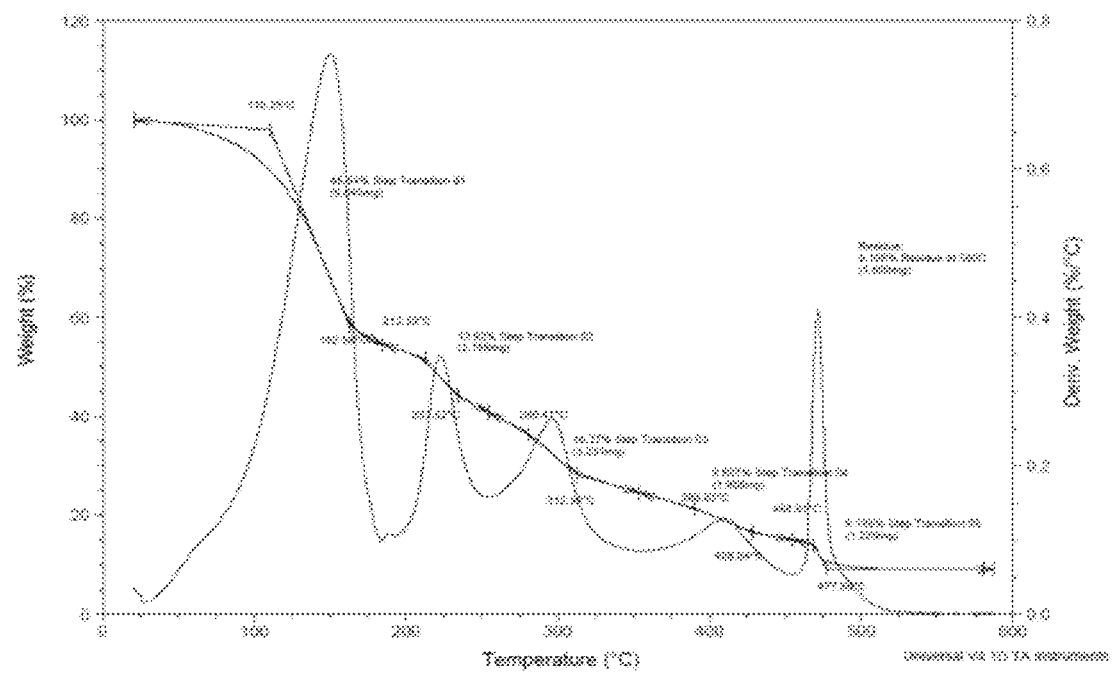
FIG. 5 shows a plot of weight loss data for a fragrance composition, described herein as example 48, from TGA. The plot shows a broad fragrance weight loss event between about 100° C. and about 160° C. The plot also shows at least four weight loss events above about 200° C. corresponding to the thermal degradation of the soy protein isolate and the viscoelastic gel.

While the disclosed fragrance composition is susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION

The compositions, materials, and methods described herein have fragrance particulates as an integral component. Fragrance particulates are a plurality of different types of individual particulates having an average particle diameter less than about 100 µm, preferably less than about 50 µm, more preferably less than about 10 µm, still more preferably less than about 5 µm, and most preferably less than about 1 µm. The average particle diameters are preferably within the range of about 0.01 µm to about 100 µm, more preferably in the range of about 0.05 µm to about 50 µm, even more preferably in the range of about 0.1 µm to about 10 µm, and still more preferably in the range of about 0.1 µm to about 2 µm. Fragrance particulates are solid or liquid, for example solid fragrances, solid fragrances encapsulated and/or entrapped by solid materials (carrier agents), solid fragrances encapsulated and/or entrapped by liquid materials (carrier agents), liquid fragrances encapsulated and/or entrapped by solid materials (carrier agents), liquid fragrances mixed with liquid materials (carrier agents), liquid fragrances, mixtures of liquid fragrances, liquid fragrance emulsion droplets, and coated fragrances entrapped within solid materials (carrier agents), and mixtures of these.

As used herein the term fragrance refers to any applicable material that is sufficiently volatile to produce a scent. Typically, fragrances are those scents pleasurable to humans, alternatively fragrances are those scents repellant to humans, animals, and/or insects. Suitable fragrances include but are not limited to fruits such as almond, apple, cherry, grape, pear, pineapple, orange, strawberry, raspberry, musk, and flower scents such as lavender-like, rose-like, iris-like, and carnation-like, but preferably, are not used as a flavoring—only as a fragrance. Other fragrances include herbal scents such as rosemary, thyme, and sage; and woodland scents derived from pine, spruce and other forest smells. Fragrances may also be derived from various oils, such as essential oils, or from plant materials such as peppermint, spearmint and the like. Fragrances can be familiar and popular smells such as baby powder, popcorn, pizza, cotton candy and the like, or can be medicinal smells and/or analgesics such as menthol, camphor, and the like. Applicable fragrances can be found in U.S. Pat. Nos. 4,534,891, 5,112,688, 5,145,842, 6,844,302 and Perfumes Cosmetics and Soaps, Second Edition, edited by W. A. Poucher, 1959, all hereby incorporated by reference. The fragrances included in these references include acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Applicable insect repellant fragrances include dichlorvos, pyrethrin, allethrin, naled and/or fenthion pesticides disclosed in the U.S. Pat. No. 4,664,064, incorporated herein by reference. Preferable insect repellants are citronellal (3,7-dimethyl-6-octanal), N,N-diethyl-3-methylbenzamide (DEET), vanillin, and the volatile oils extracted from turmeric (*Curcuma longa*), kaffir lime (*Citrus hystrix*), citronella grass (*Cymbopogon winterianus*) and hairy basil (*Ocimum americanum*). Moreover, applicable insect repellants can be mixtures of insect repellants.

The fragrance particulates applicable herein are generally not for human consumption, that is non-edible. Herein, non-edible means that the U.S. Food and Drug Administration regulates, prohibits, or has not expressly provided for their consumption. Preferably, non-edible means that one would not generally recognize the fragrance as a food stuff. Most preferably, the fragrance particulates applicable herein are human-non-toxic, non-allergenic, non-irritant, non-asthmatic, and the like.

Preferably, the fragrances used herein are hydrophobic; more preferably, the fragrance particulates used herein are hydrophobic. Herein, hydrophobic means that the fragrance (particulate) and water visibly phase separate when combined without agitation. Preferably, the fragrance (particulate) is sufficiently hydrophobic that upon sufficient agitation ("emulsification") of a mixture of the fragrance (particulate), with or without an emulsifier, and water the mixture forms an emulsion.

The breadth of applicable fragrances includes fragrances where the hydrophobicity of the fragrances varies. As a means for standardizing the hydrophobicity and the applicability of multiple fragrances and as a means for reducing the amount of fragrance in a standardized particulate size, the fragrance can be combined with one or more carrier agents.

Carrier agents are materials mixed with the selected fragrance intended to support or dilute the fragrance and aid in the formation of particulates. Carrier agents include those solvents that are capable of forming stable emulsions in water, porous polymeric materials, and solid porous particles (materials). Non-limiting examples of applicable solvents include silicon oils, paraffin fluids, vegetable oils, mineral oils, mineral waxes, vegetable waxes, and the like. These carrier agents include Isopar M (an isoparaffinic fluid) and the other Isopar variants available from ExxonMobile Corp., caprylic and capric triglycerides (e.g., NEOBEE M-5, CAS #52622-27-2; NEOBEE M-20, triglycerides of coconut oil; and NEOBEE 895, caprylic triglyceride, available from Stepan Chemicals), light mineral oils, light mineral waxes, vegetable oils, light vegetable waxes, diethylphthalate, butyl-benzoate, benzylbenzoate, ester solvents, triacetin, and glycol based water-insoluble solvents.

When the carrier agent is a solvent, the fragrance and the solvent are preferably emulsified together in an aqueous solution. Typically, the emulsification is conducted using a high shear rotor/stator homogenizer mixer like the Silverson L4RT equipped with a high sheer or emulsification screen. Typically, the Silverton mixer produces about 0.4 to about 2 micron droplets (fragrance particulates) of the carrier agent/fragrance mixture in water. The particle size can be further reduced to about 0.1 to about 1 micron through homogenization with a high pressure homogenizer like the Microfluidizer M110P from MICROFLUIDICS Inc.

Additionally, carrier agents include those materials for encapsulating a fragrance. Carrier agents can be porous polymeric or solid state materials, encapsulating shells, and the like. Examples of encapsulated fragrances include those described in U.S. patent application Ser. No. 10/823,033, filed Apr. 13, 2004, incorporated herein by reference, where the fragrances were encapsulated in substituted or un-substituted acrylic acid polymer or copolymer cross-linked with a melamine-formaldehyde pre-condensate or a urea-formaldehyde pre-condensate.

Examples of porous carrier agents for holding fragrances include various adsorbent polymeric microparticles available from AMCOL Int'l Corp., as noted below. One class of adsorbent polymeric microparticles is prepared by suspension polymerization techniques, as set forth in U.S. Pat. Nos. 5,677,407; 5,712,358; 5,777,054; 5,830,967; 5,834,577; 5,955,552; and 6,107,429, each incorporated herein by reference (available commercially under the tradename of POLY-PORE® E200, an allyl methacrylates cross polymer, from AMCOL Int'l, Arlington Heights, Ill.). Another class of adsorbent polymeric microparticle is prepared by a precipitation polymerization technique, as set forth in U.S. Pat. Nos. 5,830,960; 5,837,790; 6,248,849; and 6,387,995, each incorporated herein by reference (available commercially under the trade name of POLY-PORE® L200 from AMCOL Int'l). Yet another class of adsorbent polymeric microparticle is prepared by a precipitation polymerization technique as disclosed in U.S. Pat. Nos. 4,962,170; 4,948,818; and 4,962,133, each incorporated herein by reference. Examples of this class of absorbent polymeric microparticle are available commercially under the trade name of POLYTRAP by AMCOL Int'l (a lauryl methacrylate/glycol dimethacrylate cross polymer). Additional adsorbent polymeric microparticles have been developed, for example those disclosed in U.S. Pat. Re. 33,429, incorporated herein by reference, and sold under the trade name of MACROBEAD by AMCOL Int'l (a lauryl methacrylate/glycol dimethacrylate cross polymer). Other adsorbent polymeric microparticles that are commercially available include, for example, MICROSPONGE® (a methyl methacrylate/glycol dimethylacrylate cross polymer), as disclosed in U.S. Pat. No. 4,690,825, incorporated herein by reference, available from AMCOL Int'l, and the Poly-HIPE polymer (e.g., a copolymer of 2-ethylhexyl acrylate, styrene, and divinylbenzene) available from BIOPORE Corp., Mountain View, Calif. Additional examples of absorbent polymeric microparticles include (1) a microporous and oil sorbent microparticle comprising a terpolymer of butyl methacrylate, allyl methacrylate and an ethylene glycol dimethacrylate, in a mole ratio of about 1:3 to 5:5 to 7 respectively, said particle characterized by having a mean unit diameter of less than 25 microns and a total sorption capacity for mineral oil that is 72% by weight or greater; (2) an adsorptive polymer formed by a method of forming an adsorptive polymer by precipitation polymerization, comprising the steps of: homogeneously mixing a solution of from about 0.1 to less than 25 parts by weight of a monomer consisting exclusively of one or more types of polyunsaturated monomers, from greater than 75 to about 99.9 parts by weight of a monomer solvent, wherein the total parts of said monomers and said monomer solvent is 100 parts, and between about 0.05 to 5 weight percent free radical initiator based on the weight of said monomer, polymerizing said monomers by precipitation polymerization to form a polymer which is a combined system of particles, said particles ranging in size from 0.1 to 0.5 microns in diameter, and wherein said monomer solvent is a solvent for said monomers and a non-swelling non-solvent for said polymer, and removing said solvent from said polymer to form a dry powder; (3) a macroporous cross-linked copolymer powder capable of adsorbing hydrophilic and lipophilic fluids, comprising copolymerizing at least one monounsaturated monomer and at least one polyunsaturated monomer in the presence of an organic liquid which is a solvent for the monomers but not for the copolymer, initiating the copolymerization of the monomers by means of a free radical generating catalytic compound, precipitating a copolymer in the organic liquid in the form of a powder which includes unit particles, agglomerates, and aggregates, and forming a dry powder by removing the organic liquid from the precipitated copolymer powder, one monomer being a hydrophilic compound and the other monomer being a lipophilic compound; (4) a porous polymeric bead copolymerized from a comonomer pair selected from the groups consisting of vinyl stearate and divinylbenzene, and methylmethacrylate and ethylene glycol dimethylmethacrylate; and (5) a methacrylate/glycol dimethylacrylate cross polymer.

In another embodiment, particulate carriers include combinations of porous polymeric or solid state materials, encapsulating shells, absorbent polymeric microparticles, adsorbent polymers, and the like. One example of a fragrance particulate having a plurality of particulate carriers is an absorbent polymeric microparticle including a fragrance and within an encapsulating shell.

The amount of the carrier agent may range from about 0% to about 90% by weight of the fragrance particulate, preferably in the range from about 30% to about 80%. One or more of the foregoing fragrances is included in the fragrance particulate described herein in an amount varying from about 10% to about 100%, preferably from about 20% to about 90%, more preferably from about 30% to about 80% of the total weight of the fragrance particulate.

Methods for the general encapsulation of fragrances is known in the art, see for example U.S. Pat. Nos. 2,800,457, 3,870,542, 3,516,941, 3,415,758, 3,041,288, 5,112,688, 6,329,057, and 6,261,483, each incorporated herein by reference. Preferred encapsulating polymers include those formed from melamine-formaldehyde or urea-formaldehyde condensates, as well as similar types of aminoplasts. Additionally, capsules made by the simple or complex coacervation or emulsification of gelatin and water are also preferred for use herein. Capsules having shell walls comprised of polyurethane, polyamide, polyolefin, polysaccaharide, protein, silicone, lipid, modified cellulose, gums, polyacrylate, polyphosphazines, polystyrene, and polyesters or combinations of these materials are also applicable.

Although many variations of materials and process steps are possible, representative methods used for aminoplast encapsulation and gelatin encapsulation are disclosed in U.S. Pat. Nos. 3,516,941 and 2,800,457, respectively, each incorporated herein by reference. Both of these processes are discussed in the context of fragrance encapsulation and for use in consumer products in U.S. Pat. Nos. 4,145,184 and 5,112,688, respectively, each incorporated herein by reference.

Still more preferably, the fragrance particulate has a net charge. Herein, the net charge of the fragrance particulate can be modified by the addition of a carrier agent that itself has a net charge. Moreover, the net charge of the fragrance particulate can be increased or diluted by the addition of a carrier agent that has a neutral or net charge. Commonly, the net charge of the fragrance particulate can be determined by a measurement of the zeta ($\zeta$)-potential and/or electrophoretic mobility. Moreover, the net charge on the fragrance particulate informs the selection of materials used to coat the fragrance particulate. As will be described below, in a preferred embodiment, the first material used to coat the charged fragrance particulate has a charge opposite to that of the fragrance particulate.

Additionally, the compositions, materials, and methods described herein have a viscoelastic gel as an integral component. As used herein a viscoelastic gel is a biopolymer, polymer, copolymer, or mixture of polymer(s) and clay that exhibits viscoelastic properties in a hydrated gel state. Typically, the applicable polymers and mixtures are purchased or obtained in a solid/dried form but, upon dissolution in water form gelatinized forms. Often a mixture of the applicable polymers and mixtures and water is warmed to yield a homogeneous solution and then the mixture is cooled to gel the solution, reminiscent of making gelatin desserts, e.g., Jell-O, see U.S. Pat. No. 4,084.

Preferably, the viscoelstic gel is selected from biopolymers, synthetic polymers, copolymers of biopolymers and synthetic polymers, mixtures of biopolymers and clays and/or zeolites, mixtures of synthetic polymers and clays and/or zeolites, and mixtures of copolymers of biopolymers and synthetic polymers and clays and/or zeolites. These gels can include proteins, polysaccharides, starches, polypeptides, synthetic organic polymers, synthetic inorganic polymers, and sodium and/or calcium clays. Examples of applicable proteins are casein, whey protein, soy protein, rice protein, fish gelatin, bovine gelatin, porcine gelatin, alpha lactoglobulin, beta lactoglobulin, egg protein, albumin, and their hydrosylates. Examples of applicable polysaccharides are κ-carrageenan, ι-carrageenan, gellan gum, gelatine, chitosan, locust bean gum, guar gum (e.g., Jaguar C-17 available from Rhodia), esparto xylan, arabinoxylan, Kojac mannan, chitosan, hydroxyethyl cellulose, methylcarboxymethyl cellulose, acetyl cellulose, algenate, and pectin. Examples of synthetic organic polymers include super absorbent polymers, like polyacrylates and/or polyacylamides. Examples of synthetic inorganic polymers include sodium polyphosphates, silica xerogels, and the like. More preferably the viscoelastic gel is a polysaccharide, still more preferably the viscoelastic gel is κ-carrageenan.

As used herein the viscoelastic gel has pseudoplastic behavior, are highly elastic and solid like. Preferably, when characterized by rheometric techniques, specifically oscillatory shear, the applicable viscoelastic gels are "hard gels." The distinction between hard gel and soft gel is dependant on the storage (G') modulus of a solution of the gel. As used herein, hard gels and soft gels are distinguished by their storage modulus (G'): for hard gels, $G'>10^3$ Pa, for soft gels, $G'<10^3$ Pa. See Amphiphilic Block Copolymers: Self-Assembly and Applications 89 (Björn Lindman & Paschalis Alexandridis eds., 2000). Preferably, the visoelastic gels useful to make the fragrance-releasing products described herein have a G' of at least $10^3$ Pa, more preferably the G' of the applicable viscoelastic gels is greater than about $10^5$ Pa, still more preferably the G' of the applicable viscoelastic gels is greater than about $10^6$ Pa.

Preferably, the viscoelastic gel has a net charge (ionic charge). More preferably, when the viscoelastic gel is added directly to a fragrance particulate, the viscoelastic gel has a net charge that is opposite that of the fragrance particulate. When the fragrance particulate has a zero net charge the viscoelastic gel, still preferably, has a net charge. For example, in one embodiment, when the fragrance particulate has a net anionic charge the most useful viscoelastic gel has a net cationic charge. Without being bound to any specific theory, it is believed that the electrostatic interactions between the oppositely charged fragrance particulate and viscoelastic gel aids in the coating of the fragrance particulate with the viscoelastic gel. Additionally, it is believed that the hydrophobic nature of the fragrance particulate is a factor in the coating of the fragrance particulate with the viscoelastic gel.

Preferably, the viscoelastic gel irreversibly gels. For example, the viscoelastic gel can irreversibly gel by forming internal chemical bonds and/or by changes to the viscoelastic gel's internal physical structure. One method of irreversibly gelling the viscoelastic gel is by the addition of a cross-linking agent. Suitable cross-linking agents include calcium chloride, aldehydes, epoxides, polyaziridyl compounds, glycidyl ethers and divinyl sulfones. Preferably the cross-linking agent is calcium ions, for example from calcium chloride. Applicable cross-linking agents include salts with potassium, calcium, magnesium, sodium ions and/or other crosslinking agents such as glutaraldehyde in case of proteins, transglutaminase in case of proteins; salts such as potassium chloride, calcium chloride, calcium lactate, ferrous gluconate, copper gluconate, magnesium chloride, calcium citrate, or mixtures of these. Other methods of cross-linking the viscoelastic gel can include thermal treatment of the material, for example the thermally drive Mallard reaction, and the photochemical treatment of the material.

In another embodiment, the fragrance particulate is coated with a viscoelastic gel that has a net charge and is further coated with a second (or more) viscoelastic gel that does not have a net charge. Preferably, the fragrance particulate is coated with κ-carrageenan, and in this embodiment is further coated with a neutral polysaccharide or a mixture of neutral polysaccharides, e.g., agar, locust bean gum, xanthan gum, and/or curdlan. Without being bound to any specific theory, it is believed that the second viscoelastic gel binds or entangles with the first viscoelastic gel to form a smooth layer on the fragrance particulate. Moreover, the addition of cross-linking agents can form strong chemical interactions between two (or more) viscoelastic gels.

In yet another embodiment, the viscoelastic gel further includes a high-gelling clay. As used herein a high-gelling clay is a hydrophilic phyllosilicate, preferably a hydrophilic montmorillonite. At least three specific embodiments are available from the inclusion of a high-gelling clay in the viscoelastic gel: first, the high-gelling clay can add to or enhance the viscoelastic and gelling properties of the viscoelastic gel; second, the high-gelling clay can impart viscoelastic and gelling properties to a material that does not form a hard gel; and third, a high-gelling calcium clay can impart a cross-linking agent to the viscoelastic gel. Preferably, the high-gelling clay is a hydrophilic clay, for example sodium and/or calcium montmorillonite. More preferably, the clay is a polymer grade sodium or calcium montmorillonite, that has been ion-exchanged as described in U.S. Pat. Nos. 6,050,509 and 6,596,803, each hereby incorporated by reference, for example PGW, PGV, PGN, and PGL, all available from NANOCOR, Inc., a subsidiary of AMCOL Int'l.

In a further embodiment, the fragrance particulate is first coated with a coating agent. The coating agent may be selected from the group consisting of biopolymers, synthetic polymers, copolymers of a biopolymer and a synthetic polymer, and mixtures thereof. Examples of suitable polymers include caseins, whey proteins, soy proteins, rice proteins, fish gelatins, bovine gelatins, porcine gelatins, α-lactoglobulins, β-lactoglobulins, egg proteins, albumins, and the like. Examples of suitable biopolymers include proteins, polysaccharides, oligosaccharides, and the like. Examples of suitable synthetic polymers include hydrophobically modified polymers based on polyamines, polyimines, and the like. Preferably, the coating agent is physiochemically attracted to the fragrance particulate surface. One preferable example is when the coating agent has a charge such that the coating agent is attracted, for example through electrostatic interactions, to the fragrance particulate.

Where the fragrance particulate has a net anionic charge, the selected coating agent has a net cationic charge. Examples of coating agents with net anionic charges include anionic hydrophobically modified starches (Gum BE and HICAP 100, available from National Starch and Chemical Co., Bridgewater N.J.), starch phosphates, acetylated starch adipate, starch sodium octenyl succinate, hydroxypropyl distarch phosphate, anionic celluloses (for example sodium carboxymethylcellulose), anionically modified polysaccharides, propylene glycol alginate, gum arabic, polymers like Polyphos PPI-CO (a phosphate ester based on castor oil polyurethane in free acid form) from ALZO Chemicals, hydrophobically modified polyacrylates (like the PEMULEN series from Noveon/Lubrizol), hydrophobic lignosulfonates, humic acids, proteins above their isoelectric point at the solution pH, polyaspartates, or polyglutamates.

Examples of coating agents with net cationic charges include cationic polysaccharides, chitosan, quaternary cellulosic polymers, amidated pectines, cationically modified starches, polyquaternium 1 (CAS#: 68518-54-7); polyquaternium-2 (CAS#: 63451-27-1); polyquaternium-4 (copolymer of hydroxyethylcellulose and diallyldimethyl ammonium chloride); polyquaternium-5 (CAS#: 26006-22-4); polyquaternium-6 (polyallyldimethylammonium chloride (CAS#: 26062-79-3); polyquaternium-7 (CAS#: 26590-05-6); polyquaternium-8 (poly((methyl, stearyl) dimethylaminoethyl methacrylate), polyquaternium-9 (polydimethylaminoethylmethacrylate bromide); polyquaternium-10 (CAS#s: 53568-66-4, 55353-19-0, 54351-50-7, 81859-24-7; 68610-92-4, 81859-24-7); polyquaternium-11 (polyvinyl-N-ethylmethylpyrrolidonium); poly(ethyldimethylammonium ethylmethacrylate) sulfate copolymer), polyquaternium-12 (CAS#: 68877-50-9); polyquaternium-13 (CAS#: 68877-47-4); polyquaternium-14 (CAS#: 27103-90-8); polyquaternium-15 (CAS#: 35429-19-7); polyquaternium-16 (quaternary ammonium salt of methyl-vinylimidazolium chloride and vinylpyrrolidone) (CAS#: 95144-24-4); polyquaternium-17 (adipic acid-dimethylaminopropylamine polymer (CAS#: 90624-75-2); polyquaternium-18 (azelaic acid, dimethylaminopropylamine, dicholorethylether polymer, CAS#: 113784-58-0); polyquaternium-19 (polyvinyl alcohol, 2,3-epoxypropylamine polymer (CAS#: 110736-85-1); polyquaternium-20 (polyvinyl octadecylether, 2,3-epoxypropylamine polymer (CAS#: 110736-86-2); polyquaternium-22 (CAS#: 53694-17-0); polyquaternium-24 (hydroxyethylcellulose, lauryl dimethylammonium epoxide polymer); polyquaternium-27 (copolymer of polyquaternium-2 and polyquaternium-17, CAS#: 131954-48-4); polyquaternium- 28 (vinylpyrrolidone, dimethylaminopropylmethacrylamide copolymer, CAS#: 131954-48-8), polyquaternium-29 (chitosan, CAS#: 9012-76-4); propylene oxide polymer reacted with epichlorohydrin); polyquaternium-30 (methylmethacrylate, methyl(dimethylacetylammonium ethyl)acrylate copolymer, (CAS#: 147398-77-4); polyquaternium-33 (CAS#: 69418-26-4); poly(ethylene(dialkyl)ammonium) polymethacrylamidopropyltrimonium chloride (CAS#: 68039-13-4); and poly(2-acryloyloxyethyl)trimethylammonium).

Preferably, the coating agent has a weight average molecular weight less than about 1,000,000 Daltons, more preferably less than about 500,000 Dalton, even preferably less than about 300,000 Dalton, and still more preferably less than about 100,000 Dalton. Still more preferably, the molecular weight of the coating agent is balanced against the size of the fragrance particulate, where the larger the fragrance particulate the higher the preferred molecular weight, the smaller the fragrance particulate the lower the preferred molecular weight. For example, for a fragrance particulate having a size of about 0.1 μm the preferred molecular weight of the coating agent is about 50,000 Daltons; for a fragrance particulate having a size of about 2 μm the preferred molecular weight of the coating agent is about 500,000 Daltons. Without being bound to theory, it is hypothesized that larger polymeric coating agents do not form cohesive layers over small fragrance particulates.

More preferably the coating agent is Soy Protein Isolate, which is a highly refined or purified form of soy protein with a minimum protein content of 90% on a moisture-free basis. It is made from defatted soy flour which has had most of the non-protein components, fats and carbohydrates removed.

In the embodiments described herein, wherein the fragrance particulate is first coated with a coating agent, the selected viscoelastic gel should have a net charge that is opposite to that of the coating agent. For example, when the fragrance particulate is coated with a cationic soy protein isolate, a preferred viscoelastic gel is an anionic κ-carrageenan. Coating agents with a net charge provide a mechanism for the addition of the viscoelastic gel to the coated fragrance particulate. Without being bound to theory, the charged viscoelastic gel can physiochemically interacts with the coating agent via for example electrostatic interactions, covalent bonding between amino and carboxylic groups present in the biopolymers in the two layers under high heat prolonged processing conditions, e.g., a Maillard reaction, disulfide bond formation among biopolymers containing excess SH bonds in the two layers, condensation reactions, hydrogen bonding, and/or hydrophobic interactions among the hydrophobic groups.

Following the coating of the fragrance particulate, and/or the coating of the fragrance particulate that was first coated with a coating agent, with at least one viscoelastic gel, the fragrance composition is homogenized by extrusion or other homogenization techniques known in the art and, optionally, further coated with one or more polymeric materials.

Preferably, the homogenized fragrance composition is then dried by spray drying, drum drying, oven drying, vacuum drying, and the like. When the fragrance composition is oven dried, the temperature is preferably below about 60° C., more preferably at about 50° C. When the fragrance composition is spray dried the spray dryer inlet temperature is between about 150° C. and about 175° C. When the fragrance composition is vacuum dried the applied vacuum is about 150 to about 50 mm Hg, preferably about 125 to about 50 mm Hg. The dried fragrance composition can then be ground, chopped, or sized to a desired particle size. Preferably, the fragrance composition is dried to a moisture content of less than about 25 wt. % water, more preferably less than about 20 wt. %, even more preferably less than about 15 wt. %., still more preferably less than about 10 wt. %.

When the fragrance composition is oven dried at 50° C., 50 wt. % or more of the fragrance added to the composition is retained in the dry product, preferably 70 wt. % or more of the fragrance is retained, even more preferably 80 wt. % or more is retained, still more preferably 85 wt. % or more is retained, and still more preferably 90 wt. % or more is retained. Alternatively, when the fragrance composition is spray dried, often less than 80% of the fragrance added is retained. When the fragrance composition is further treated with a shell forming polymer, e.g., an acrylate polymer (e.g., Resyn 28-2930 and/or Amphomer from National Starch), and is then spray dried the retention of fragrance is enhanced to at least 50%, preferably to at least 70%, more preferably to at least 80%, even more preferably to at least 85%, and still more preferably to at least 90%.

In still another embodiment, the dried and sized fragrance composition particles can be further coated with one or more layers of polymers, oligomers, and/or small molecules that provide a deposition and/or adhesion benefit (herein called deposition aids) that aid to deposit the fragrance deposition composition on the intended substrate, e.g., teeth, hair, skin, fabric, plastic, polymer, glass, stone, metal, insects, plants, fungus, yeast, and foods.

In one embodiment, the deposition aid is a combination of two polymers herein termed a Type-1 Polymer and a Type-2 Polymer. Preferably, the fragrance composition particles are coated first with the Type-1 Polymer and then with the Type-2 Polymer, as described in application Ser. No. 12/397,043, filed Mar. 3, 2009, hereby incorporated by reference. The Type-1 Polymer is a polymer having a cationic atom (e.g., cationic nitrogen) content in the range of about 3 to about 20 wt. % and a weight average molecular weight in the range of about 300,000 to 800,000 Dalton. The Type-1 Polymer can be a homopolymer or a copolymer including an amphiphilic polymer or copolymer, a hydrophobically-modified polymer or copolymer, and the like. The preferred Type-1 cationic polymer is poly(diallyldimethyl ammonium halide), poly (DADMAC). The Type-2 Polymer is a polymer having a cationic atom (e.g., cationic nitrogen) content of about 0.1 to about 3 wt. % and a weight average molecular weight greater than about 1,000,000 Dalton. The Type-2 Polymer can be a cationic guar gum, a cationic cellulose, a cationic starch, hydrophobically-modified versions of the foregoing, or the like.

Preferably, the deposition aides are cationic polymers that have a moderate to low cationic charge content. As used herein the cationic charge content is measured by the cationic atom content. The cationic atom content is a measure of the total atomic weight of the atoms bearing cationic charge in/on the polymer chain divided by the molecular weight of the polymer, times 100, expressed as a weight percentage. By way of descriptive example, all of the cationic nitrogen atoms in the polymer poly(diallyldimethyl ammonium halide), poly (DADMAC), are quaternary ammonium ions, thereby the cationic atom content (here, the cationic nitrogen content) can be determined either by elemental analysis of a sample of the poly(DADMAC) or by the weight average molecular weight of the polymer. The elemental analysis would provide the weight percentage of nitrogen atoms in a sample of polymer which is the cationic atom content.

Preferably, the deposition aids used herein have cationic atom contents of less than about 3 wt. %. More preferably, the deposition aids have cationic atom contents in the range of about 0.01 wt. % to about 3 wt. %, still more preferably in the range of about 0.1 wt. % to about 2 wt. %, and even more preferably in the range of about 0.5 wt. % to about 1 wt. %. Additionally, deposition aids, preferably, have a weight average molecular weight in the range of about 1,000,000 to about 15,000,000 Dalton, more preferably in the range of about 1,000,000 to about 10,000,000 Dalton, and still more preferably in the range of about 1,000,000 to about 5,000,000 Dalton.

In yet another embodiment, the dried and sized fragrance composition particles can be emulsified in an water immiscible fluid. Preferably, the water immiscible fluid is a silicone fluid, silicone gel, silicone wax, petroleum fluid, petroleum gel, petroleum wax, vegetable oil, vegetable wax, paraffin wax, a hydrophobic organic liquid, and/or a mixture thereof. When the water immiscible fluid is a wax, the wax preferably melts in a range from about 30° C. to about 55° C. These water immiscible fluid emulsified fragrance composition particulates are preferably dispersed in the water immiscible fluid phase through the use of a dispersant, where the dispersant supports the distribution of the hydrophilic fragrance composition in the hydrophobic water immiscible fluid. Often the dispersant is necessary in this embodiment because the fragrance composition particulates are hydrophilic and are typically immiscible with water immiscible fluid. Following the dispersion of the fragrance composition particulates in oil, the oil emulsion is then emulsified in water. The dispersant is preferably water insoluble such as Lauryl PEG-9 Polydimethyl siloxyethyl dimethicone (KF-6038 from Shin Etsu), Polyderm PPI-SA soyamine polymer, other dimethicone based emulsifiers like dimethicone copolyols, aminosilicones, or may be water soluble silicone-quat from Evonik, such as Rewoquat SQ1. The water immiscible fluid particulates dispersed in the water can then be coated by a deposition aid as described in Ser. No. 12/397,043, filed Mar. 3, 2009. These depositions aids incorporate the Type-1 and Type-2 polymers described above and an inorganic polymer. The inorganic polymers are selected from water-soluble or water-dispersible anionic polymers, such as polyphosphate, polysulfonates (e.g., polyvinyl sulfonate, lignosulfonates), polycarboxylates (e.g. sodium polyacrylate), polysulfates (e.g., polyvinyl sulfate), and silicone polymers with a pendant anionic group selected from carboxylate, sulfate, and phosphate groups. Preferably, the anionic polymer is sufficiently surface-active for adsorption at an oil-water interface, capable of reducing the surface tension of water, when added at a level of 1% by weight, preferably reducing the surface tension by at least 15%.

A preferred anionic polymer is a water-insoluble but oil-soluble, liquid copolymer of castor oil phosphate and 3-isocyanatomethyl-3,5,5-trimethyl cyclohexyl isocyanate, referred to herein as castor oil phosphate/IPDI copolymer. This anionic polymer is preferred because of its relatively low solubility (2 weight % or lower in surfactant solutions containing 3 weight % or higher amount of surfactant) in surfactant solutions, and because the liquid form is expected to yield less rigid (i.e., softer) cationic particles used as the emulsifier in accordance with the present invention.

In still another embodiment, the fragrance composition is entrapped within a larger porous second carrier agent. As used herein, the second carrier agent can be the same material(s) and/or formulation(s) as the above recited porous carrier agents but the relative size of the second carrier agent must be sufficiently large to entrap the fragrance composition. Examples of preferred second carrier agents include MICROSPONGE, POLYTRAP or POLYPORE available from AMCOL Int'l Corp., microcrystalline cellulose, e.g., AVICEL PH200 NF available from FMC Biopolymers, and zeolites.

Often the loading of the second carrier agent with the fragrance composition requires the fragrance composition to be added as a hydrated form. As the hydrated forms of fragrances contain large amounts of water, a repetitive, loading-drying procedure was developed to increase the overall loading of the fragrance composition within the second carrier agent, despite the high water content of hydrated fragrances. Briefly, the hydrated fragrance composition is admixed with the second carrier agent and then the mixture is dried preferably to a moisture content less than about 15 wt. % (yielding a first product), additional hydrated fragrance composition is then admixed with the first product and the mixture is dried, preferably to a moisture content less than about 15 wt. % to yield a second product having an increased fragrance percentage. This procedure may be continued until the desired concentration of the fragrance composition in the second carrier agent is obtained or until the second carrier agent can no longer adsorb more fragrance composition.

This second carrier agent composition can then be dispersed in oil and treated as above; can be used as a powder; or can be itself coated with the above disclosed materials. Preferably, the second carrier agent composition is dispersed in silicone oil and then coated with a deposition aid (as disclosed above), thereby providing a composition that imparts both a fragrance and a softening effect.

In still another embodiment, a second fragrance particulate (the same or different from the fragrance particulate described above) is added to the viscoelastic gel to form a gel-embedded fragrance. Preferably, the gel-embedded fragrance is different from the fragrance particulate described above. More preferably, the gel-embedded fragrance contains at least one cross-linking agent. Even more preferably, the gel-embedded fragrance is added to a wet fragrance composition after the viscoelastic gel has physiochemically attached to the fragrance particulate described above, before or after the viscoelastic gel has set. Theoretically and preferably, the second fragrance (in the gel-embedded fragrance) is released from the total composition first, thereby allowing for single compositions that smell differently at under different processing or at different times.

Yet another aspect of the fragrance particulate materials, compositions and methods described herein is the incorporation of the fragrance particulate materials in commercial products. The fragrance particulate materials can be used in products such as shampoos, soaps, body washes, laundry detergents, fabric softeners, toothpastes, and antiseptic ointments. Those commercial products that contain coated fragrance particulate materials can, particularly further include solvents and/or other ingredients such as detergent or cleansing surfactants. Examples of solvents and/or added ingredients include fatty alcohols, opacifiers, pearlescers, viscosity modifiers, rheology modifiers, inorganic oxides, buffering or pH adjusting chemicals, foam-boosters, perfumes, dyes, coloring agents or pigments, herb extracts, preservatives, hydrotopes, enzymes, bleaches, fabric conditioners, optical brighteners, antioxidants, stabilizers, thickeners, dispersants, soil release agents, anti-wrinkle agents, polymers, chelants, anti-corrosion agents, teeth cleansing and whitening agents, polymers, copolymers, cross-polymers, smectite clays, silica, silicate minerals, and the like. Generally, these products employ cleansing or detergent surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134, each hereby incorporated by reference. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562, each hereby incorporated by reference. Liquid laundry detergents which can use the fragrance-releasing compositions described herein include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818, each hereby incorporated by reference. Shampoo and conditioners that can employ the fragrance-releasing compositions described herein include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090, 4,705,681, each hereby incorporated by reference.

Non-limiting examples of suitable detergent or cleansing anionic surfactants that can be combined with the herein described fragrance particulate compositions are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Non-limiting examples of detergent or cleansing nonionic surfactants that can be combined with the herein described fragrance particulate composition include, but are not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides. Non-limiting examples of detergent or cleansing amphoteric surfactants that can be combined with the herein described fragrance-releasing particulate compositions include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms. Nonlimiting examples of suitable cationic surfactants that can be combined with the herein described fragrance particulate composition include water-soluble or water-dispersible or water-insoluble compounds containing at least one amine group which is preferably a quaternary amine group, and at least one hydrocarbon group which is preferably a long-chain hydrocarbon group. The hydrocarbon group may be hydroxylated and/or alkoxylated and may comprise ester- and/or amido- and/or aromatic-groups. The hydrocarbon group may be fully saturated or unsaturated. Generally, the surfactant is combined with the fragrance particulate composition in a range from about 1 to about 95%, preferably from about 2 to about 90%, and most preferably from 3 to 90% by weight of the total compositions.

Alternatively the fragrance particulate compositions described herein can be formed into a commercial product by admixing the fragrance particulate composition with a hydrophilic solvent. Suitable hydrophilic solvents include water, glycerol, ethanol, isopropanol, propylene glycol, butylene glycol, hexylene glycol, polyethylene glycol and mixtures thereof. Generally, the solvent is combined with the fragrance particulate composition in a range from about 0.1 to about 95%, preferably from 1 to 90%, and most preferably from 3 to 90% by weight of the total compositions.

EXAMPLES

The following examples more fully illustrate preferred embodiments within the scope of the present invention. The following examples are provided to illustrate the invention, but are not intended to limit the scope thereof.

General ranges for components of the preferred embodiments are presented in Table 1. These weight percent ranges signify the weight percent of the component in a wet gel composition, as made clear below. Table 1 lists both necessary and optional components and provides ranges for the inclusion of these components in the fragrance composition (wet gel composition).

TABLE 1

| Components | Range (%) |
| --- | --- |
| Fragrance | 2-7 |
| Viscoelastic Gel (e.g., κ-carrageenan) | 0.5-3 |
| Coating Agent (e.g., Soy Protein Isolate) | 0.5-1 |
| DI Water | 60-90 |
| 0.5 M aqueous citric acid | 0.5-2.4 |
| Cross-linking Agent | |
| 0.15 M Calcium chloride soln. | 0.5-3 |
| Sodium Benzoate | 0.01-1 |
| Potassium Chloride | 0.5-3 |
| Propylene Carbonate | 1-3 |
| Sodium Montmorillonite Clay | 0.1-5 |
| Organoclay | 5-10 |

Representative preparation of a viscoelastic gel coated fragrance particulate.

In a two liter beaker was combined 15 g of soy protein isolate, Supro EX 39 (available from SOLAE Co.) and 900 g of deionized (DI) water. The aqueous solution was vigorously mixed with a Silverson L4RT rotor/stator mixer equipped with a round emulsifier screen (5,000-6,000 rpm for 20-30 min). To this aqueous mixture was then added 90 g of a lavender fragrance (available from BELL FLAVORS & FRAGRANCES as 44% active fragrance in Isopar M) and this mixture was emulsified for 30 min at 6,000-7,000 rpm. Next, 18.81 g of a 0.5 M aqueous citric acid solution was added and the mixture was further mixed for 5 min. This coated fragrance particulate was then slowly added to a pre-made solution of 45 g of κ-carrageenan (Gelcarin 911 NF available from FMC BIOPOLYMERS) in 1500 g water that was warmed to fully dissolve the κ-carrageenan and then maintained at about 50° C. The mixture of the coated fragrance particulate and the viscoelastic gel was maintained at 50° C. for about one hour, calcium chloride was then added, the mixture stirred for 10 min, then sodium benzoate was added as an aqueous solution, the mixture was stirred for 5 minutes, and then refrigerated for 12-24 hours. The gelatinous mass was then extruded and dried at about 50° C. for 24-48 hours. The dried fragrance composition was then ground in a Retsch grinder and then screened through a 0.5 mm mesh.

The following wet formulation examples were prepared using methods analogous to the representative example provided above without the drying step:

| Example 1 | Mass (g) | Wt. % |
|---|---|---|
| DI water | 600 | 34.9 |
| Soy protein isolate | 10 | 0.6 |
| Lavender fragrance, 44% active, rest Isopar M | 60 | 3.5 |
| 0.5 M aqueous citric acid | 9.65 | 0.6 |
| κ-carrageenan | 30 | 1.7 |
| DI water | 1000 | 58.2 |
| 0.15 M Calcium chloride soln. | 10 | 0.6 |
| Total | 1719.65 | 100 |

| Example 2 | Mass (g) | Wt. % |
|---|---|---|
| DI water | 1000 | 37.3 |
| Soy protein isolate | 15 | 0.6 |
| Lemondet fragrance, 100% active | 90 | 3.4 |
| 0.5 M aqueous citric acid | 15.93 | 0.6 |
| κ-carrageenan | 45 | 1.7 |
| DI water | 1500 | 56.0 |
| 0.15 M Calcium chloride soln. | 15 | 0.6 |
| Total | 2680.93 | 100 |

| Example 3 | Mass (g) | Wt. % |
|---|---|---|
| DI water | 900 | 32.5 |
| Soy protein isolate | 15 | 0.5 |
| 90 gm Lemondet fragrance, 100% active, in 180 g Avicel PH 200 NF | 270 | 9.7 |
| 0.5 M aqueous citric acid | 16.12 | 0.6 |
| κ-carrageenan | 45 | 1.6 |
| DI water | 1500 | 54.1 |
| 0.15 M Calcium chloride soln. | 25 | 0.9 |
| Total | 2771.12 | 100 |

| Example 4 | Mass (g) | Wt. % |
|---|---|---|
| DI water | 900 | 34.7 |
| Soy protein isolate | 15 | 0.6 |
| Lavendet fragrance, 100% active | 90 | 3.5 |
| 0.5 M Citric acid soln. | 18.19 | 0.7 |
| κ-carrageenan | 45 | 1.7 |
| DI water | 1500 | 57.8 |
| 0.15 M Calcium chloride soln. | 25 | 1.0 |
| Total | 2593.19 | 100 |

| Example 5 | Mass (g) | Wt. % |
|---|---|---|
| DI water | 900 | 34.4 |
| Soy protein isolate | 18.3 | 0.7 |
| Lavendet fragrance, 100% active | 110 | 4.2 |
| 0.5 M Citric acid soln. | 18.77 | 0.7 |
| κ-carrageenan | 22.5 | 0.9 |
| ι-carrageenan, Gelcarin 379 | 22.5 | 0.9 |
| DI water | 1500 | 57.3 |
| 0.15 M Calcium chloride soln. | 25 | 1.0 |
| Total | 2617.07 | 100 |

| Example 6 | Mass (g) | Wt. % |
|---|---|---|
| DI water | 900 | 33.9 |
| Soy protein isolate | 15 | 0.6 |
| Floral high boiling point fragrance, 100% active | 90 | 3.4 |
| 0.5 M Citric acid soln. | 27.81 | 1.1 |
| κ-carrageenan | 45 | 1.7 |
| DI water | 1500 | 56.4 |
| 0.15 M Calcium chloride soln. | 80 | 3.0 |
| DI water | 50 | 1.9 |
| Sodium benzoate | 5.24 | 0.2 |
| Total | 2657.81 | 100 |

| Example 7 | Mass (g) | Wt. % |
|---|---|---|
| DI water | 900 | 33.9 |
| Soy protein isolate | 15 | 0.6 |
| Floral high boiling point fragrance, 100% | 90 | 3.4 |
| 0.5 M Citric acid soln. | 49.87 | 1.9 |
| κ-carrageenan | 22.5 | 0.9 |
| ι-carrageenan | 22.5 | 0.9 |
| DI water | 1500 | 56.5 |
| 0.15 M Calcium chloride soln. | 80 | 3.0 |
| DI water | 50 | 1.9 |
| Sodium benzoate | 5.24 | 0.2 |
| Total | 2657.37 | 33.9 |

| Example 8 | Mass (g) | Wt. % |
|---|---|---|
| DI water | 900 | 33.9 |
| Soy protein isolate | 15 | 0.6 |
| Floral high boiling point fragrance, 100% | 90 | 3.4 |
| 0.5 M Citric acid soln. | 27.81 | 1.1 |
| ι-carrageenan | 45 | 1.7 |
| DI water | 1500 | 56.4 |
| 0.15 M Calcium chloride soln. | 80 | 3.0 |
| DI water | 50 | 1.9 |
| Sodium benzoate | 5.32 | 0.2 |
| Total | 2657.81 | 33.9 |

| Example 9 | Mass (g) | Wt. % |
|---|---|---|
| DI water | 900 | 34.6 |
| Soy protein isolate | 15 | 0.6 |
| Lavender fragrance, 44% active, rest Isopar M | 90 | 3.5 |
| 0.5 M Citric acid soln. | 29.88 | 1.2 |
| κ-carrageenan | 45 | 1.7 |
| DI water | 1500 | 57.6 |
| 0.15 M Calcium chloride soln. | 25 | 1.0 |
| Total | 2604.88 | 100 |

| Example 10 | Mass (g) | Wt. % |
|---|---|---|
| DI water | 900 | 34.7 |
| Soy protein isolate | 15 | 0.6 |
| Lavender fragrance, 44% active, rest Isopar M | 90 | 3.5 |
| 0.5 M Citric acid soln. | 18.81 | 0.7 |
| κ-carrageenan | 45 | 1.7 |
| DI water | 1500 | 57.8 |
| 0.15 M Calcium chloride soln. | 25 | 1.0 |
| Total | 2593.81 | 100 |

| Example 11 | Mass (g) | Wt. % |
|---|---|---|
| DI water | 900 | 34.0 |
| Soy protein isolate | 15 | 0.6 |
| Lavender fragrance, 70% active, rest Isopar M | 90 | 3.4 |
| 0.5 M Citric acid soln. | 18.28 | 0.7 |
| κ-carrageenan | 45 | 1.7 |
| DI water | 1500 | 56.6 |
| 0.15 M Calcium chloride soln. | 25 | 0.9 |
| DI water | 50 | 1.9 |
| Sodium Benzoate | 5.19 | 0.2 |
| Total | 2648.47 | 100 |

| Example 12 | Mass (g) | Wt. % |
|---|---|---|
| DI water | 900 | 34.0 |
| Soy protein isolate | 15 | 0.6 |
| Lavender fragrance, 100% active | 90 | 3.4 |
| 0.5 M Citric acid soln. | 19.83 | 0.8 |
| κ-carrageenan | 45 | 1.7 |
| DI water | 1500 | 56.6 |
| 0.15 M Calcium chloride soln. | 25 | 0.9 |
| DI water | 50 | 1.9 |
| Sodium Benzoate | 5.19 | 0.2 |
| Total | 2650.02 | 100 |

| Example 13 | Mass (g) | Wt. % |
|---|---|---|
| DI water | 900 | 34.0 |
| Soy protein isolate | 15 | 0.6 |
| Lavender fragrance, 11% active, rest Isopar M | 90 | 3.4 |
| 0.5 M Citric acid soln. | 19.71 | 0.7 |
| κ-carrageenan | 45 | 1.7 |
| DI water | 1500 | 56.6 |
| 0.15 M Calcium chloride soln. | 25 | 0.9 |
| DI water | 50 | 1.9 |
| Sodium Benzoate | 5.18 | 0.2 |
| Total | 2649.89 | 100 |

| Example 14 | Mass (g) | Wt. % |
|---|---|---|
| DI water | 900 | 34.0 |
| Soy protein isolate | 15 | 0.6 |
| Lavender fragrance, 70% active, rest Isopar M | 90 | 3.4 |
| 0.5 M Citric acid soln. | 20.27 | 0.8 |
| κ-carrageenan | 45 | 1.7 |
| DI water | 1500 | 56.6 |
| 0.15 M Calcium chloride soln. | 25 | 0.9 |
| DI water | 50 | 1.9 |
| Sodium Benzoate | 5.18 | 0.2 |
| Total | 2650.45 | 100 |

| Example 15 | Mass (g) | Wt. % |
|---|---|---|
| DI water | 600 | 21.5 |
| Soy protein isolate | 29 | 1.0 |
| Lavender fragrance, 100% active | 60 | 2.2 |
| 0.5 M Citric acid soln. | 54.71 | 2.0 |
| κ-carrageenan | 60 | 2.2 |
| DI water | 1900 | 68.0 |
| 0.15 M Calcium chloride soln. | 33.33 | 1.2 |
| DI water | 50 | 1.8 |
| Sodium Benzoate | 5.45 | 0.2 |
| Total | 2792.49 | 100 |

| Example 16 | Mass (g) | Wt. % |
|---|---|---|
| DI water | 900 | 46.1 |
| Soy protein isolate | 12 | 0.6 |
| Lavender fragrance, 70% active, rest Isopar M | 129 | 6.6 |
| 0.5 M Citric acid soln. | 13.5 | 0.7 |
| κ-carrageenan | 20 | 1.0 |
| DI water | 800 | 41.0 |
| 0.15 M Calcium chloride soln. | 25 | 1.3 |
| DI water | 50 | 2.6 |
| Sodium Benzoate | 3.78 | 0.2 |
| Total | 1953.28 | 100 |

| Example 17 | Mass (g) | Wt. % |
|---|---|---|
| DI water | 900 | 46.0 |
| Soy protein isolate | 12 | 0.6 |
| Lavender fragrance, 70% active, rest Isopar M | 129 | 6.6 |
| 0.5 M Citric acid soln. | 15.51 | 0.8 |
| κ-carrageenan | 20 | 1.0 |
| DI water | 800 | 40.9 |
| 0.15 M Calcium chloride soln. | 25 | 1.3 |
| DI water | 50 | 2.6 |
| Sodium Benzoate | 3.78 | 0.2 |
| Total | 1955.29 | 100 |

| Example 18 | Mass (g) | Wt. % |
|---|---|---|
| DI water | 900 | 33.6 |
| Soy protein isolate | 15 | 0.6 |
| HVF, 100% active | 90 | 3.4 |
| 0.5 M Citric acid soln. | 16.55 | 0.6 |
| κ-carrageenan | 45 | 1.7 |
| DI water | 1500 | 55.9 |
| 0.15 M KCl | 30 | 1.1 |
| 0.15 M Calcium chloride soln. | 60 | 2.2 |
| DI water | 50 | 1.9 |
| Sodium Benzoate | 5.31 | 0.2 |
| Total | 2681.86 | 100 |

| Example 19 | Mass (g) | Wt. % |
|---|---|---|
| DI water | 500 | 19.0 |
| Soy protein isolate | 26 | 1.0 |
| HVF, 100% active | 72 | 2.7 |
| 0.5 M Citric acid soln. | 62.89 | 2.4 |
| κ-carrageenan | 52 | 2.0 |
| DI water | 1800 | 68.5 |
| 0.15 M KCl | 30 | 1.1 |

| Example 19 | Mass (g) | Wt. % |
| --- | --- | --- |
| 0.15 M Calcium chloride soln. | 60 | 2.3 |
| DI water | 50 | 1.9 |
| Sodium Benzoate | 5.236 | 0.2 |
| Total | 2628.126 | 100 |

| Example 20 | Mass (g) | Wt. % |
| --- | --- | --- |
| DI water | 900 | 44.9 |
| Soy protein isolate | 12 | 0.6 |
| HVF, 100% active | 129 | 6.4 |
| 0.5M Citric acid soln. | 31.83 | 1.6 |
| κ-carrageenan | 20 | 1.0 |
| DI water | 800 | 39.9 |
| 0.15 M KCl | 30 | 1.5 |
| 0.15 M Calcium chloride soln. | 60 | 3.0 |
| DI water | 50 | 2.5 |
| Sodium Benzoate | 3.87 | 0.2 |
| Total | 2006.7 | 100 |

| Example 21 | Mass (g) | Wt. % |
| --- | --- | --- |
| DI water | 900 | 45.3 |
| Soy protein isolate | 12 | 0.6 |
| HVF, 100% active, loaded in Microsponge porous carrier, 10-20 microns - (160 g fragrance in 100 g microsponge = 61.5% loading) | 129 | 6.5 |
| 0.5 M Citric acid soln. | 11.86 | 0.6 |
| κ-carrageenan | 20 | 1.0 |
| DI water | 800 | 40.3 |
| 0.15 M KCl | 30 | 1.5 |
| 0.15 M Calcium chloride soln. | 60 | 3.0 |
| DI water | 50 | 2.5 |
| Sodium Benzoate | 3.826 | 0.2 |
| Total | 1986.686 | 100 |

| Example 22 | Mass (g) | Wt. % |
| --- | --- | --- |
| DI water | 900 | 33.4 |
| Soy protein isolate | 15 | 0.6 |
| LVF, 100% active | 90 | 3.3 |
| 0.5 M Citric acid soln. | 31.2 | 1.2 |
| κ-carrageenan | 45 | 1.7 |
| DI water | 1500 | 55.6 |
| 0.15 M KCl | 30 | 1.1 |
| 0.15 M Calcium chloride soln. | 60 | 2.2 |
| DI water | 50 | 1.9 |
| Sodium Benzoate | 5.34 | 0.2 |
| Total | 2696.54 | 100 |

| Example 23 | Mass (g) | Wt. % |
| --- | --- | --- |
| DI water | 500 | 19.1 |
| Soy protein isolate | 26 | 1.0 |
| LVF, 100% active | 72 | 2.8 |
| 0.5 M Citric acid soln. | 48.5 | 1.9 |
| κ-carrageenan | 52 | 2.0 |
| DI water | 1800 | 68.9 |
| 0.15 M KCl | 30 | 1.2 |

| Example 23 | Mass (g) | Wt. % |
| --- | --- | --- |
| 0.15 M Calcium chloride soln. | 60 | 2.3 |
| DI water | 50 | 1.9 |
| Sodium Benzoate | 5.26 | 0.2 |
| Total | 2613.76 | 100 |

| Example 24 | Mass (g) | Wt. % |
| --- | --- | --- |
| DI water | 900 | 45.0 |
| Soy protein isolate | 12 | 0.6 |
| LVF, 100% active | 129 | 6.5 |
| 0.5 M Citric acid soln. | 24.73 | 1.2 |
| κ-carrageenan | 20 | 1.0 |
| DI water | 800 | 40.0 |
| 0.15 M KCl | 30 | 1.5 |
| 0.15 M Calcium chloride soln. | 60 | 3.0 |
| DI water | 50 | 2.5 |
| Sodium Benzoate | 3.85 | 0.2 |
| Total | 1999.58 | 100 |

| Example 25 | Mass (g) | Wt. % |
| --- | --- | --- |
| DI water | 900 | 45.2 |
| Soy protein isolate | 12 | 0.6 |
| LVF, 100% active, loaded in Microsponge porous carrier, 10-20 microns - (160 g fragrance in 100 g microsponge = 61.5% loading) | 129 | 6.5 |
| 0.5 M Citric acid soln. | 18.53 | 0.9 |
| κ-carrageenan | 20 | 1.0 |
| DI water | 800 | 40.1 |
| 0.15 M KCl | 30 | 1.5 |
| 0.15 M Calcium chloride soln. | 60 | 3.0 |
| DI water | 50 | 2.5 |
| Sodium Benzoate | 3.84 | 0.2 |
| Total | 1993.37 | 100 |

| Example 26 | Mass (g) | Wt. % |
| --- | --- | --- |
| DI water | 154 | 17.7 |
| Soy protein isolate | 8 | 0.9 |
| LVF, 44% active, solvent is Neobee M5 | 22.15 | 2.5 |
| 0.5 M Citric acid soln. | 11.46 | 1.3 |
| κ-carrageenan | 16 | 1.8 |
| DI water | 585 | 67.2 |
| 0.15 M KCl | 11.08 | 1.3 |
| 0.15 M Calcium chloride soln. | 22.15 | 2.5 |
| DI water | 50 | 5.7 |
| Sodium Benzoate | 1.65 | 0.2 |
| Total | 870.41 | 100 |

| Example 27 | Mass (g) | Wt. % |
| --- | --- | --- |
| DI water | 154 | 17.7 |
| Soy protein isolate | 8 | 0.9 |
| LVF, 44% active, solvent is Neobee M20 | 22.15 | 2.6 |
| 0.5 M Citric acid soln. | 11.05 | 1.3 |
| κ-carrageenan | 16 | 1.8 |
| DI water | 585 | 67.2 |
| 0.15 M KCl | 11.08 | 1.3 |
| 0.15 M Calcium chloride soln. | 22.15 | 2.6 |

-continued

| Example 27 | Mass (g) | Wt. % |
|---|---|---|
| DI water | 50 | 5.7 |
| Sodium Benzoate | 1.66 | 0.2 |
| Total | 870.01 | 100 |

| Example 28 | Mass (g) | Wt. % |
|---|---|---|
| DI water | 154 | 17.7 |
| Soy protein isolate | 8 | 0.9 |
| LVF, 44% active, in Diethylphthalate | 22.15 | 2.6 |
| 0.5 M Citric acid soln. | 9.22 | 1.1 |
| κ-carrageenan | 16 | 1.8 |
| DI water | 585 | 67.4 |
| 0.15 M KCl | 11.08 | 1.2 |
| 0.15 M Calcium chloride soln. | 22.15 | 2.6 |
| DI water | 50 | 5.7 |
| Sodium Benzoate | 1.66 | 0.2 |
| Total | 868.18 | 100 |

| Example 29 | Mass (g) | Wt. % |
|---|---|---|
| DI water | 154 | 17.8 |
| Soy protein isolate | 8 | 0.9 |
| LVF, 44% active, rest Isopar M | 22.15 | 2.6 |
| 0.5 M Citric acid soln. | 8.47 | 1.0 |
| κ-carrageenan | 16 | 1.8 |
| DI water | 585 | 67.4 |
| 0.15 M KCl | 11.08 | 1.3 |
| 0.15 M Calcium chloride soln. | 22.15 | 2.6 |
| DI water | 50 | 5.7 |
| Sodium Benzoate | 1.66 | 0.2 |
| Total | 867.43 | 100 |

Examples 1-29 were then dried. Drying was by either oven drying at 50° C. or by spray drying at a nozzle inlet temperature of approximately 170° C. The amount and characteristics of the fragrance in the dried samples was then determined by gas chromatography. The standard methods used are outlined below but any analytical chromatographic technique is applicable.

GC Method for Determining the Nature and Amount of Fragrance in Composition

Fragrance compositions were tested by gas chromatography (GC) on an Agilent Technologies 6890 N GC system having a 7683 Agilent series injector. The general GC conditions were:

| | |
|---|---|
| Column | HP-5 30 m, 0.25 mm, 0.25 um (19091J-433) |
| Initial Temp | 60° C. |
| Initial Time | 2 min |
| Ramp: | 8 C/min to 200 then 20 C/min to 280, hold 8 min |
| Inlet Temp | 240° C. |
| Flow Rate ml/min | 1.2, constant flow |
| Carrier gas | He |
| Detector Temp, C. | 280 |
| Detector | FID |
| Gas | Hydrogen = 40 ml/min, Air = 450 ml/min |
| Injection Volume, | 1 μl |
| Split Ratio | 50:1 |

A calibration curve was run for each individual fragrance every day with standards prepared at different concentrations in pure ethanol. Compositions prepared according to the current disclosure were tested by dissolving 1 g of the fragrance composition in 50 ml of ethanol, heating the ethanolic solution to 55° C. for 2 h with stirring, sonicating the solution for about 30 min, and then centrifuging the solution at 2000 RPM for 15 min. The ethanolic supernatant was then filtered through 0.2 micron filter and then injected into the gas chromatography instrument. The filtrate, above, was treated again with ethanol in the same manner as detailed above and the supernatant from this second extraction was also analyzed by gas chromatography. The weight percentage of the fragrance in the dry product was then calculated against the standardization curves and known amount of dry product analyzed.

| | Wet Sample | Oven Dried 50° C. | Spray Dried 170° C. | Fragrance Wt. % added | Fragrance Wt. % in dry product |
|---|---|---|---|---|---|
| Ex. 30. | Ex. 1 | X | | 26.11 | 16.79 |
| Ex. 31. | Ex. 2 | X | | 59.30 | 47.50 |
| Ex. 32. | Ex. 3 | X | | 27.11 | 10.60 |
| Ex. 33. | Ex. 4 | X | | 59.15 | 47.40 |
| Ex. 34. | Ex. 5 | X | | 62.75 | not tested |
| Ex. 35. | Ex. 6 | X | | 56.50 | 55.80 |
| Ex. 36. | Ex. 7 | X | | 55.76 | 44.60 |
| Ex. 37. | Ex. 8 | X | | 56.49 | 54.60 |
| Ex. 38. | Ex. 9 | X | | 58.71 | not tested |
| Ex. 39. | Ex. 10 | X | | 26.01 | 23.60 |
| Ex. 40. | Ex. 10 | | X | 26.00 | 12.35 |
| Ex. 41. | Ex. 11 | X | | 40.03 | 30.49 |
| Ex. 42. | Ex. 11 | | X | 41.36 | 7.0 |
| Ex. 43. | Ex. 12 | X | | 57.14 | 47.00 |
| Ex. 44. | Ex. 12 | | X | 59.01 | 10.0 |
| Ex. 45. | Ex. 13 | X | | 6.29 | 6.00 |
| Ex. 46. | Ex. 14 | X | | 12.57 | 9.90 |
| Ex. 47. | Ex. 15 | X | | 37.44 | 18.20 |
| Ex. 48. | Ex. 16 | X | | 54.24 | 47.75 |
| Ex. 49. | Ex. 17 | | X | 54.17 | 9.0 |
| Ex. 50. | Ex. 18 | X | | 56.87 | 50.50 |
| Ex. 51. | Ex. 19 | X | | 44.28 | 39.20 |
| Ex. 52. | Ex. 20 | X | | 76.21 | 72.50 |
| Ex. 53. | Ex. 21 | X | | 47.04 | 39.40 |
| Ex. 54. | Ex. 22 | X | | 56.62 | 52.41 |
| Ex. 55. | Ex. 23 | X | | 44.66 | 38.88 |
| Ex. 56. | Ex. 24 | X | | 76.52 | 71.10 |
| Ex. 57. | Ex. 25 | X | | 48.12 | 40.50 |
| Ex. 58. | Ex. 26 | X | | 19.73 | 15.32 |
| Ex. 59. | Ex. 27 | X | | 19.74 | 18.18 |

Additional examples include fragrance combined with organoclays then coated with a coating agent, and next coated with a viscoelastic gel. The procedure for the preparation of this example is analogous to the representative preparation provided above, but the fragrance was first admixed with the organoclay and then coated with the soy protein isolate. The following formulation represents one such example:

| Example 60 | Mass (g) | Wt. % |
|---|---|---|
| DI water | 300 | 20.8 |
| Soy protein isolate | 14.5 | 1.0 |
| Propylene carbonate | 1.58 | 0.1 |
| Organo clay (Organo 34, AMCOL Intl.) | 7.92 | 0.6 |
| Lavender fragrance, 100% active | 39.1 | 2.7 |
| 0.5 M Citric acid soln. | 18.53 | 1.3 |
| κ-carrageenan | 30 | 2.1 |
| DI water | 950 | 65.7 |
| 0.15 M Calcium chloride soln. | 40.38 | 2.8 |
| 0.15 M KCl soln. | 20.2 | 1.4 |
| DI water | 50 | 3.5 |
| Sodium Benzoate | 2.85 | 0.2 |
| Total | 1445.36 | 100 |

| | Wet Sample | Oven Dried 50° C. | Spray Dried 170° C. | Fragrance Wt. % added | Fragrance Wt. % in dry product |
|---|---|---|---|---|---|
| Ex. 61 | Ex. 65 | X | | 39.6 | 29.4 |
| Ex. 62 | Ex. 65 | | X | 39.6 | 10.3 |

Additional examples include the addition of clay to the viscoelastic gel coated fragrance particulate. The procedure for the preparation of this example is analogous to the representative preparation provided above, where the clay is added to the admixed fragrance particulate and viscoelastic gel with a cross-linking agent. In this example the clay was entrapped within the viscoelastic gel. The following formulation represents one such example:

| Example 63 | Mass (g) | Wt. % |
|---|---|---|
| DI water | 250 | 18.4 |
| Soy protein isolate | 14.5 | 1.1 |
| Lavender fragrance, 100% active | 30 | 2.2 |
| 0.5 M Citric acid soln. | 17.97 | 1.3 |
| κ-carrageenan | 20 | 1.5 |
| DI water | 950 | 69.7 |
| 0.15 M Calcium chloride soln. | 26.92 | 2.0 |
| 0.15 M KCl soln. | 13.47 | 1.0 |
| 25% PGV-5 clay pregel in DI water | 40 | 2.9 |
| DI water | 50 | 3.6 |
| Sodium Benzoate | 2.72 | 0.2 |
| Total | 1362.11 | 100 |

| | Wet Sample | Oven Dried 50° C. | Spray Dried 170° C. | Fragrance Wt. % added | Fragrance Wt. % in dry product |
|---|---|---|---|---|---|
| Ex. 64 | Ex. 63 | X | | 37.65 | 35.90 |

Additional examples include the addition of a microparticulate to the viscoelastic gel coated fragrance particulate; in the example formulation, below, the microparticulate is the fragrance entrapped within the MICROSPONGE. While in this formulation the fragrance of the microparticulate and the fragrance of the fragrance particulate are the same, the fragrances can be the same or different. One of ordinary skill would recognize that dependant on the volatility of the fragrances used this multiple fragrance delivery could produce multiple scents over time. The procedure for the preparation of this example is analogous to the representative preparation provided above, where the microparticulate is added to the admixed fragrance particulate and viscoelastic gel with a cross-linking agent. In this example the microparticulate was entrapped within the viscoelastic gel. The following formulation represents one such example:

| Example 65 | Mass (g) | Wt. % |
|---|---|---|
| DI water | 250 | 18.4 |
| Soy protein isolate | 14.5 | 1.1 |
| Lavender fragrance, 100% active | 30 | 2.2 |
| 0.5 M Citric acid soln. | 17.97 | 1.3 |
| κ-carrageenan | 20 | 1.4 |
| DI water | 950 | 69.7 |
| 0.15 M Calcium chloride soln. | 26.92 | 2.0 |
| 0.15 M KCl soln. | 13.47 | 1.0 |
| Microsponge | 5.32 | 0.4 |
| Lavender fragrance, 100% active | 6.9 | 0.5 |
| 5% CaCl$_2$ solution | 2.78 | 0.2 |
| DI water | 50 | 3.6 |
| Sodium Benzoate | 2.68 | 0.2 |
| Total | 1362.07 | 100 |

| | Wet Sample | Oven Dried 50° C. | Spray Dried 170° C. | Fragrance Wt. % added | Fragrance Wt. % in dry product |
|---|---|---|---|---|---|
| Ex. 66 | Ex. 65 | X | | 44.98 | 40.60 |

Example 67

In yet another example the fragrance composition is loaded into or entrapped within a porous solid. One method for making an entrapped fragrance composition is by the dispersion of a wet gel composition, e.g., Examples 1-29, in water and the addition of a porous solid. The addition of the fragrance composition to the porous solid can be done as a single step, or can be done step wise with the drying of the entrapped fragrance composition prior to the further addition of the wet gel composition. The stepwise addition of the wet fragrance composition to the porous solid can yield a final entrapped fragrance composition with a higher fragrance concentration, in part because the volume occupied by the wet gel prevents the further inclusion of fragrance composition in single step additions. Alternatively, the wet gel composition can be added to the porous solid prior to gellation. A standard formulation was prepared according to the Representative Preparation:

| Standard Formulation | Mass (g) | Wt. % |
|---|---|---|
| DI water | 500 | 18.7 |
| Soy protein isolate | 29 | 1.1 |
| Lavender fragrance, 100% active | 60 | 2.2 |
| 0.5 M Citric acid soln. | 36.02 | 1.4 |
| κ-carrageenan | 60 | 2.2 |
| DI water | 1900 | 71.1 |
| 0.15 M Calcium chloride soln. | 33.33 | 1.3 |
| DI water | 50 | 1.9 |
| Sodium Benzoate | 5.24 | 0.2 |
| Total | 2673.59 | 100 |

This standard formulation was then added to MICROSPONGE 5640 (available from AMCOL Int'l) by the methods discussed above. The wet addition involved the addition of 180 g of the standard formulation to 360 g water and the rapid mixing of the mixture with a Silverson mixer fitted with a fine emulsion screen for 20 min. The standard formulation was admixed with the porous carrier three times with the material being dried after each addition. The general parameters for the additions are:

|                                      | 1st loading | 2nd loading | 3rd loading |
|---|---|---|---|
| Microsponge 5640 (g)                 | 30.74  | —      | —      |
| Loaded MS 5640 Used (g, Dry)         | —      | 27.19  | 28.26  |
| Wet Gel Solution Added (g)           | 60.55  | 63.91  | 41.32  |
| Mix Time (Minutes)                   | 20     | 20     | 20     |
| Time Dried at 50 C. (Hours)          | 17 Hours | 12 Hours | 19 Hours |
| Dry Weight After Drying (g)          | 27.85  | 28.26  | 28.49  |
| Theoretical fragrance conc.          |        |        | 3.90%  |
| Final analytical fragrance conc.     |        |        | 3.60%  |

Example 68

In another example the standard formulation was added to the porous carrier prior to the gellation of the viscoelastic gel. The standard formulation was admixed with MICROSPONGE 5640 (available from AMCOL Int'l) at 50° C. The mixture was allowed to set at about 5° C., and then was dried at about 50° C. The general parameters for the preparation of this example are:

| | |
|---|---|
| Microsponge 5640 Used (g)           | 50.00  |
| Mass of Standard Formulation Added (g) | 78.67 |
| Mix Time (Minutes)                  | 20     |
| Time to Set (Hours)                 | 22     |
| Wet Weight (g)                      | 126.85 |
| Time Dried at 50° C. (Hours)        | 15     |
| Weight After Drying (g)             | 51.83  |
| Theoretical fragrance conc.         | 3.2%   |
| Final analytical fragrance conc.    | 3.1%   |

TGA Method for Determining Thermal Stability

The thermogravimetric analysis (TGA) of dry fragrance compositions was carried out on a TA Instruments TGA 2950. Generally, about 20 mg a sample was heated at 10° C./min from 25° C. to 600° C. Dried fragrance compositions were tested by TGA to determine weight loss onset temperatures. The weight loss onset temperature is indicative of the loss of fragrance components and theoretically a change in the fragrance profile with the processing of the compositions. Higher thermal stability, as determined by a higher weight loss onset temperature, suggests that commercial products employing the herein described fragrance compositions require release mechanisms other than thermal desorption.

DSC Method for Determining Preferred Fragrance Concentrations

Figure 6:
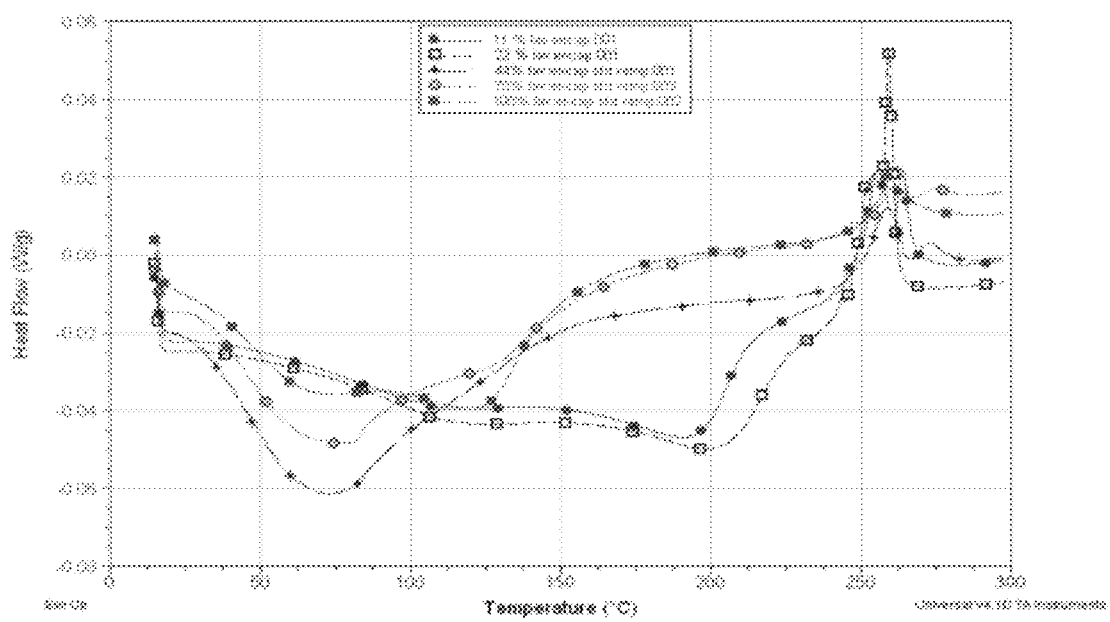
FIG. 6 is compilation of plots of digital scanning calorimetry (DSC) data from samples of the herein described fragrance compositions where the samples vary in the weight percentage of fragrance in the fragrance particulate; examples 39, 41, 43, 45, and 46. The plots of the 100 wt. % and the 70 wt. % samples show two endothermic events between about 50° C. and about 150° C. with the higher temperature event being indicative of excess (free) fragrance. Without being bound to theory, the event at about 75° C., seen in the plots for the 100 wt. %, 70 wt. % and 44 wt. % samples, is believed to be caused by a polymer softening event. The plot of the 22 wt. % and 11 wt. % samples show an endothermic event at about 200° C. that is believed to be due in part to a decomplexation of the fragrance from the carrier agent. Notably, the 44 wt. % sample shows a single endothermic event below 200° C. indicative of a homogeneous composition.
Figure 7:
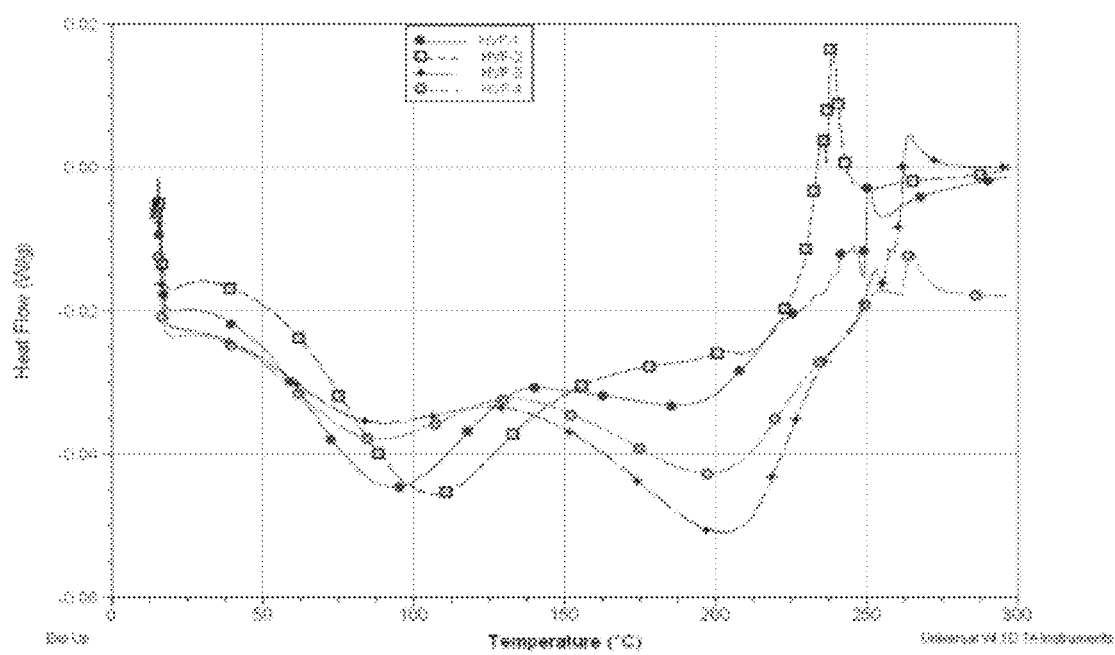
FIG. 7 is a compilation of plots of DSC data from samples of the herein described fragrance compositions where the samples vary in the application of the coating agent. Samples correspond to examples 50-53.
Figure 8:
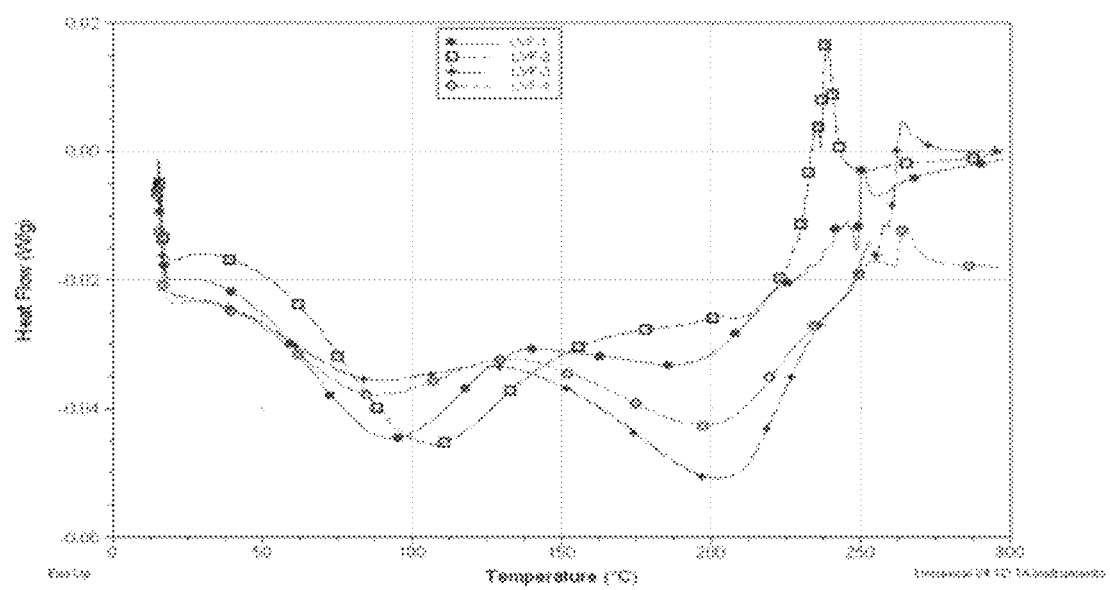
FIG. 8 is a compilation of plots of DSC data from samples of the herein described fragrance compositions where the samples vary in the application of the coating agent. Samples correspond to examples 54-57.
Figure 9:
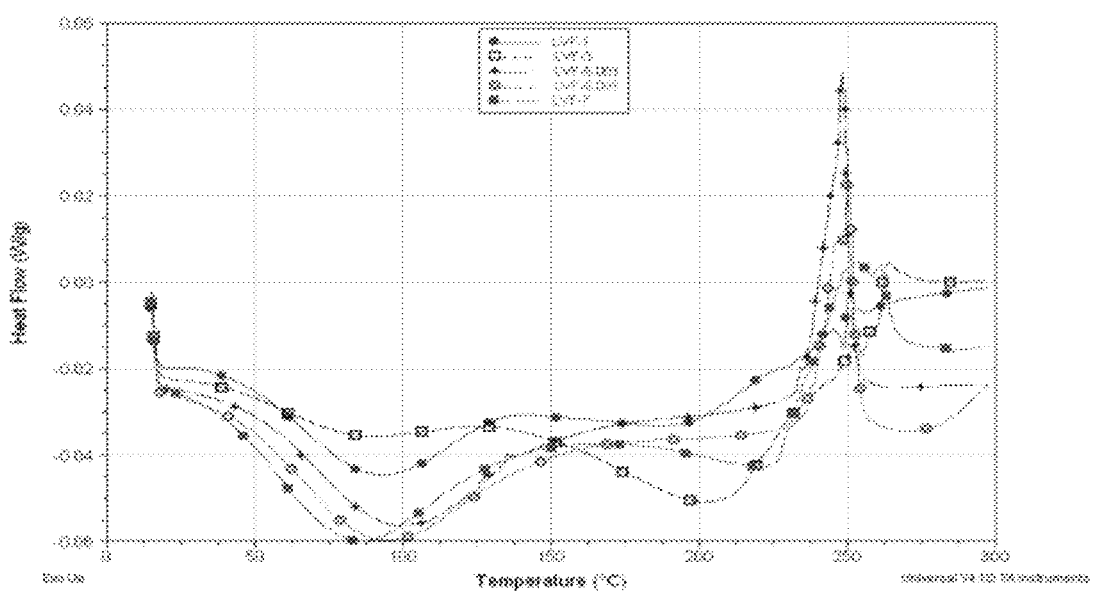
FIG. 9 is a compilation of plots of DSC data from samples of the herein described fragrance compositions where the fragrance particulate in one sample is 100 wt. % fragrance and the fragrance particulates in the remaining samples are 44 wt. % fragrance with the balance being a carrier agent, where the carrier agents are varied between samples; examples 58-61. The results shown correspond to NEOBEE M5, NEOBEE M20, diethyl phthalate, and ISOPAR M.
Figure 10:
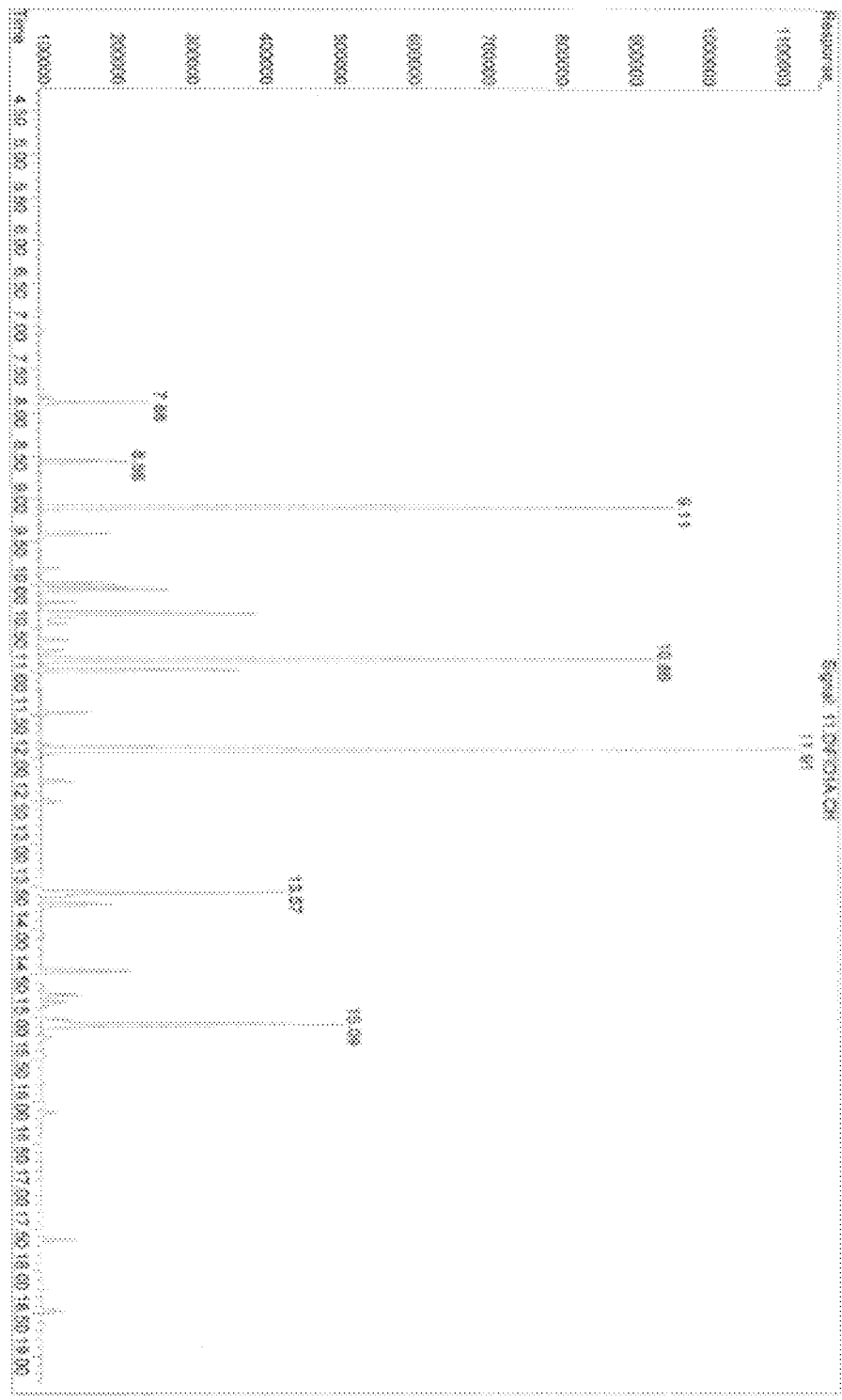
FIG. 10 shows gas chromatography (GC) data from a sample of neat lavender fragrance. The peaks are indicative of the different chemical compounds contained in the fragrance, where the presence of the chemical compounds and ratio between the compounds determines how the fragrance is perceived.
Figure 11:
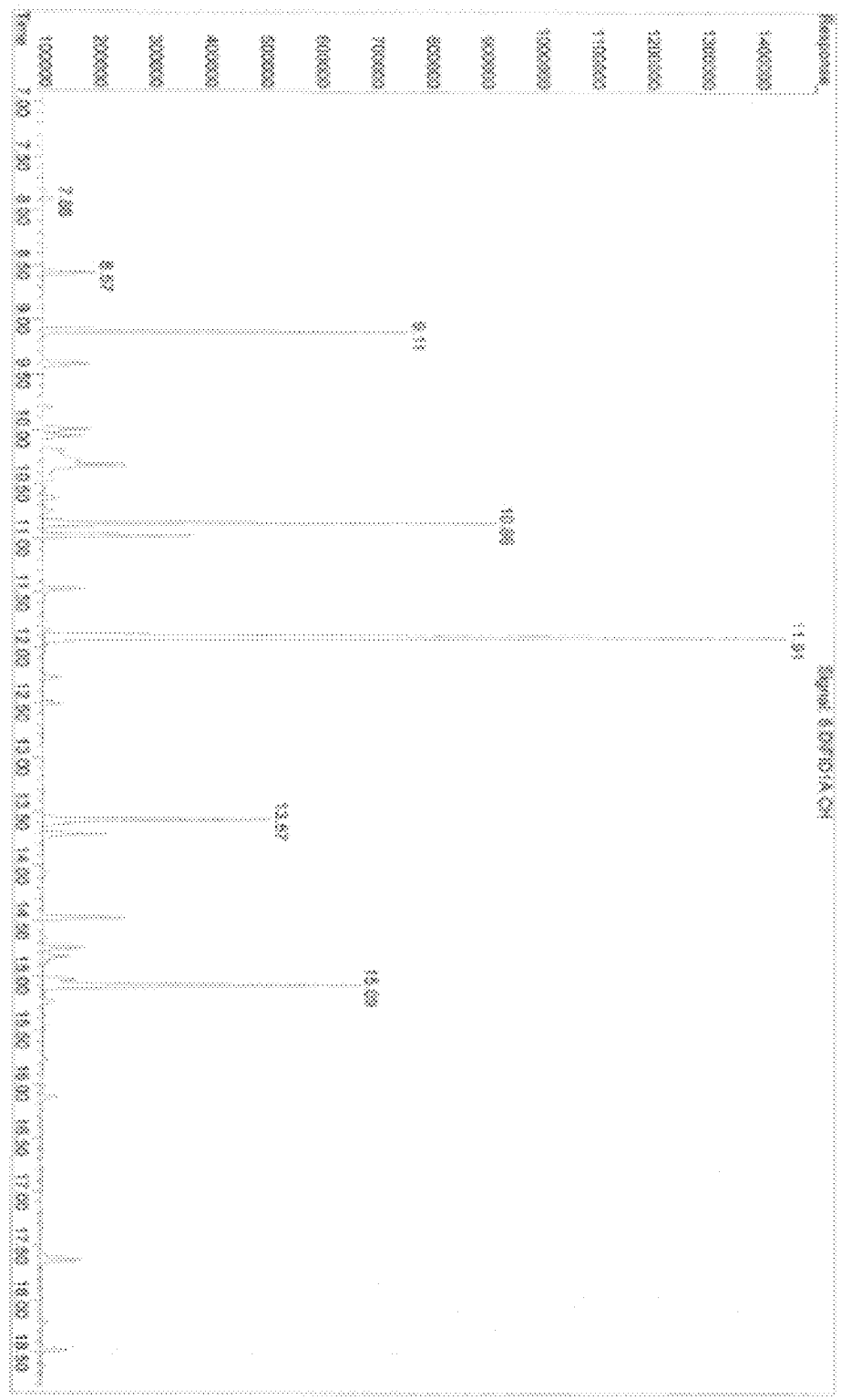
FIG. 11 shows GC data from an sample extracted from a dried (lavender) fragrance composition; example 43. Notably and in comparison to FIG. 10, the same peaks appear in approximately the same ratio.
Figure 12:
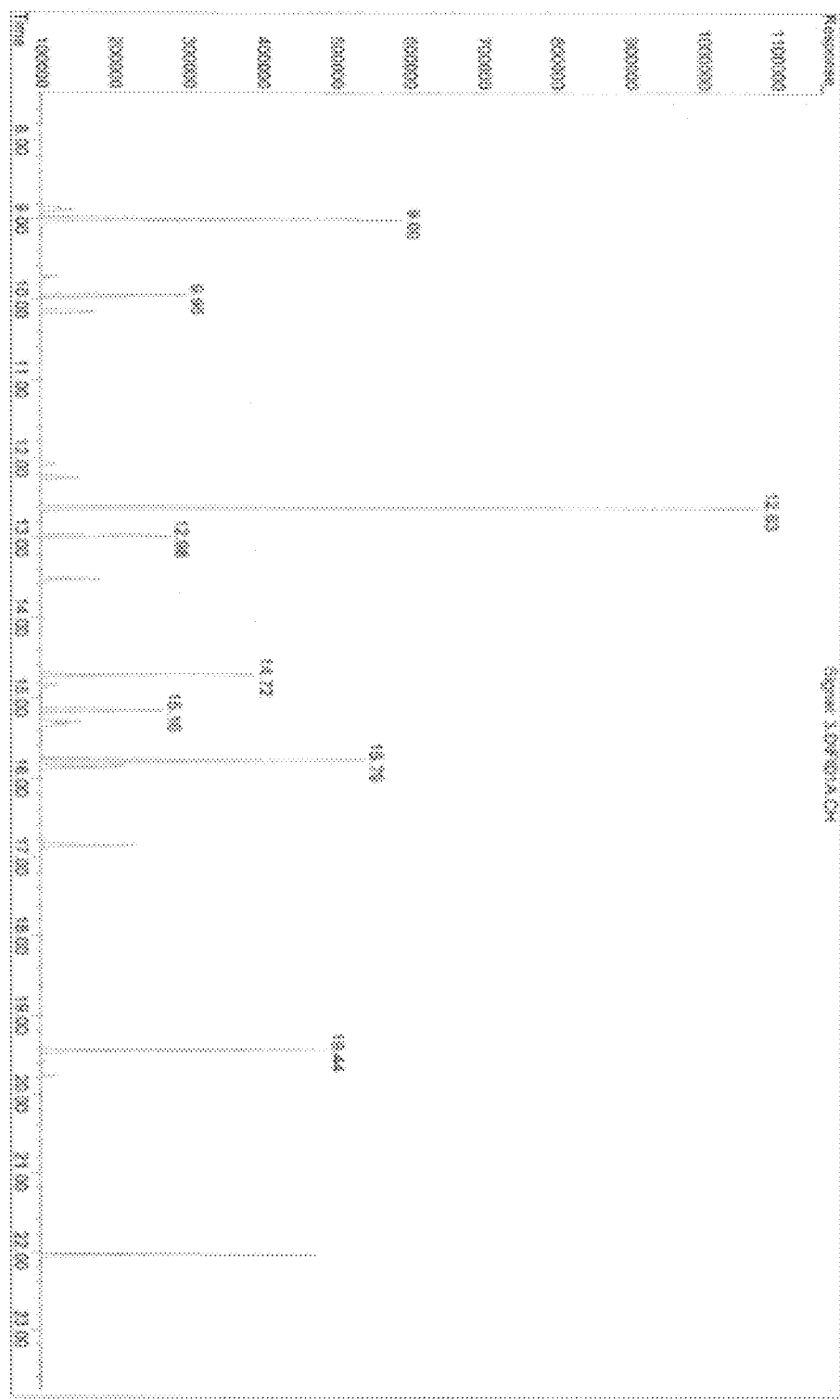
FIG. 12 shows gas chromatography (GC) data from a sample of neat apple fragrance, a low volatility fragrance. The peaks are indicative of the different chemical compounds contained in the fragrance, where the presence of the chemical compounds and ration between the compounds determines how the fragrance is perceived.
Figure 13:
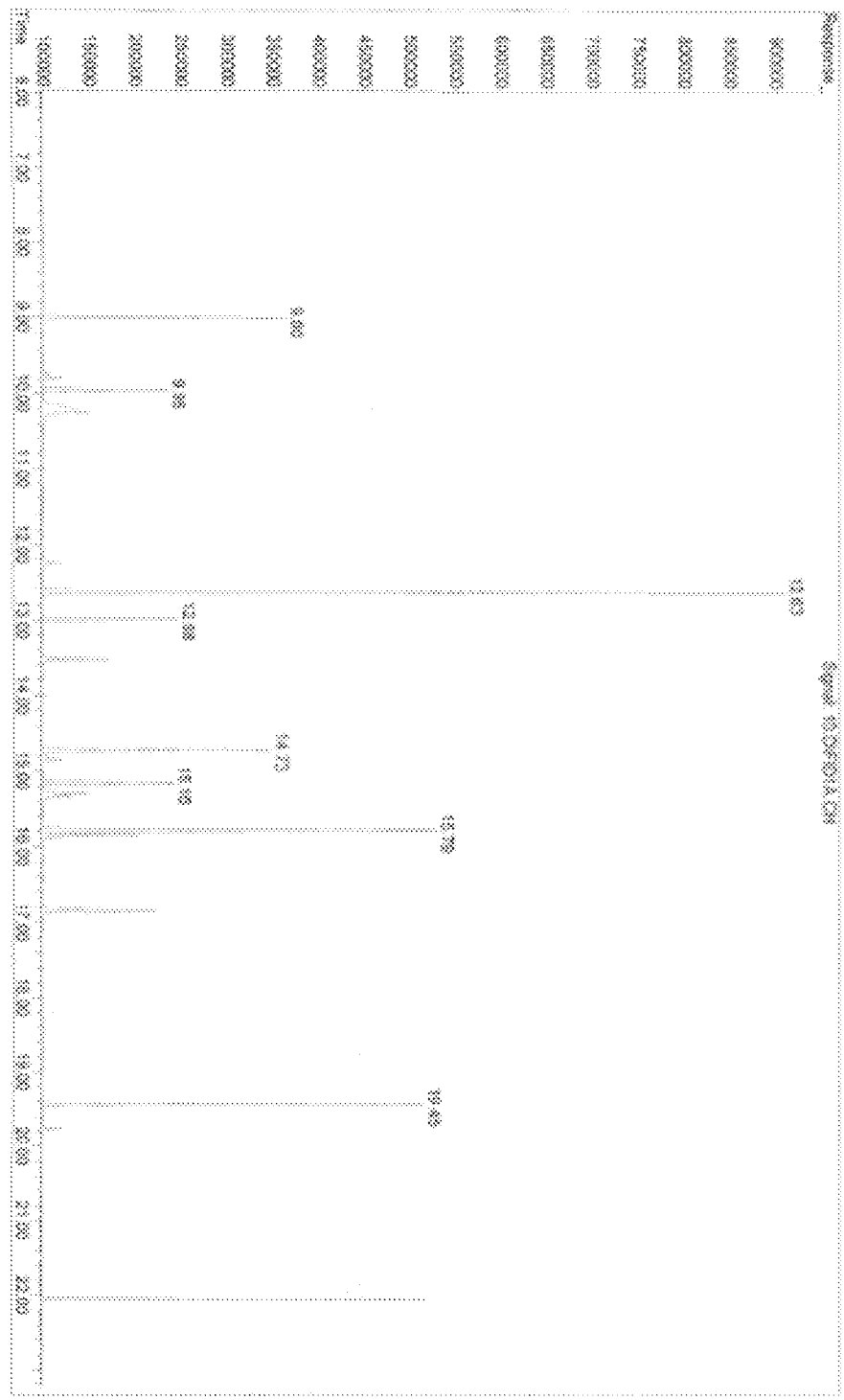
FIG. 13 shows GC data from an sample extracted from a dried (apple) fragrance composition. Notably and in comparison to FIG. 12, the same peaks appear in approximately the same ratio.

Digital scanning calorimetry ("DSC") data were obtained with a TA Instruments Q100 model with a ramp program at 10° C./min. The samples were about 4-6 mg and were tested in non-hermetically sealed pans. Low temperature endothermic events in the DSC data correspond to known evaporation/boiling points of the non-polymeric materials within the compositions. Often changes in the formulation of the composition changes the endothermic events; these changes are believed to correspond to the presence of "excess" fragrance (see FIG. 6 at about 125° C.) or strong complexation of the fragrance (see FIG. 6 at about 200° C.). Preferably, excess fragrance is minimized in fragrance compositions due to the cost of the fragrance and the potential loss of the excess fragrance during processing.

Representative Example for the Preparation of a Coated Fragrance Particulate for Consumer Application.

Additional examples were prepared where the above described examples were admixed with a water immiscible fluid and then treated with deposition aids, similar to copending U.S. application Ser. No. 12/327,570, incorporated herein for the process of coating water immiscible fluids with polymeric deposition aids. The samples including water immiscible fluids were prepared with a standard mixed polymer solution having an anionic polymer and a Type-1 polymer and a standard solution having a Type-2 polymer. The preparation of the standard solutions are presenting in the copending application. The general formulations are presented below:

| Mixed Polymer Standard Solution | Mass (g) | Wt. % |
|---|---|---|
| 50% NaOH solution | 10.5 | 0.4 |
| Polyphos PPI-CO IPDI copolymer(Alzo Chemicals) | 60 | 2.4 |
| DI water | 1073.5 | 42.9 |
| Poly(DADMAC) | 1350 | 54 |
| Glydant | 6 | 0.2 |
| Total | 2500 | 100 |
| Zetag 7122: PPI-CO |  | 4.5 |

| Type-2 Polymer Standard Solution | Mass (g) | Wt. % |
|---|---|---|
| Deionized water | 956.6 | 95.6 |
| Jaugar C-17 | 32.6 | 3.2 |
| Phosphoric acid, 85% | 0.8 | 0.1 |
| Phenonip | 10 | 1 |
| Total | 1000 | 100 |

One method of preparing samples for testing and/or consumer application includes admixing the fragrance composition with a water immiscible fluid. Then emulsifying the mixture in water and admixing with the mixed polymer standard solution. Next, the Type-2 polymer solution is admixed with the mixture. Generally, samples were prepared by mixing a dry fragrance composition with a water immiscible fluid, and emulsifying in water. The emulsified materials was then admixed with a Mixed Polymer Standard Solution, which was followed by admixing with adding a Type-2 Polymer Standard Solution. The final fragrance composition was then isolated and dried. Formulations for some samples are provided:

Example 69

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |
| Example 50 | 51.106 | 43.7 |
| Organo 34 organoclay, AMCOL Intl. | 10.212 | 8.7 |
| Propylene Carbonate | 2.047 | 1.7 |
| Total | 116.971 | 100 |

| Deposition-Aid treated fragrance composition | Amount, gm | % by weight |
|---|---|---|
| Water Immiscible Fluid phase | 113.51 | 35.1 |
| Mixed Polymer Standard Solution | 127.83 | 39.5 |
| Deionized water | 0 | 0.0 |

-continued

| Deposition-Aid treated fragrance composition | Amount, gm | % by weight |
|---|---|---|
| Type-2 Polymer Standard Solution | 81.72 | 25.3 |
| Deionized water | 0 | 0.0 |
| Total | 323.06 | 100 |
| Amount of fragrance in isolated composition | | 7.8 |

Example 70

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |
| Example 51 | 51.106 | 43.7 |
| Organo 34 organoclay, AMCOL Intl. | 10.212 | 8.7 |
| Propylene Carbonate | 2.047 | 1.8 |
| Total | 116.971 | 100 |

| Deposition-Aid treated fragrance composition | Amount, gm | % by weight |
|---|---|---|
| Water Immiscible Fluid phase | 115.86 | 34.4 |
| Mixed Polymer Standard Solution | 136.46 | 40.5 |
| Deionized water | 0 | 0 |
| Type-2 Polymer Standard Solution | 84.5 | 25.1 |
| Deionized water | 0 | 0 |
| Total | 323.06 | 100 |
| Amount of fragrance in isolated composition | | 5.89 |

Example 71

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |
| Example 52 | 51.106 | 43.7 |
| Organo 34 organoclay, AMCOL Intl. | 10.212 | 8.7 |
| Propylene Carbonate | 2.047 | 1.8 |
| Total | 116.971 | 100 |

| Deposition-Aid treated fragrance composition | Amount, gm | % by weight |
|---|---|---|
| Water Immiscible Fluid phase | 121.28 | 35.1 |
| Mixed Polymer Standard Solution | 136.678 | 39.6 |
| Deionized water | 0 | 0 |
| Type-2 Polymer Standard Solution | 87.32 | 25.3 |
| Deionized water | 0 | 0 |
| Total | 345.278 | 100 |
| Amount of fragrance in isolated composition | | 11.8 |

Example 72

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |
| Example 53 | 51.106 | 43.7 |
| Organo 34 organoclay, AMCOL Intl. | 10.212 | 8.7 |
| Propylene Carbonate | 2.047 | 1.7 |
| Total | 116.971 | 100 |

| Deposition-Aid treated fragrance composition | Amount, gm | % by weight |
|---|---|---|
| Water Immiscible Fluid phase | 116.73 | 36.5 |
| Mixed Polymer Standard Solution | 119.22 | 37.3 |
| Deionized water | 0 | 0.0 |
| Type-2 Polymer Standard Solution | 84.05 | 26.3 |
| Deionized water | 0 | 0.0 |
| Total | 320 | 100 |
| Amount of fragrance in isolated composition | | 6.28 |

Example 73

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |
| Example 54 | 51.106 | 43.7 |
| Organo 34 organoclay, AMCOL Intl. | 10.212 | 8.7 |
| Propylene Carbonate | 2.047 | 1.7 |
| Total | 116.971 | 100 |

| Deposition-Aid treated fragrance composition | Amount, gm | % by weight |
|---|---|---|
| Water Immiscible Fluid phase | 113.21 | 35.4 |
| Mixed Polymer Standard Solution | 125 | 39.1 |
| Deionized water | 0 | 0.0 |
| Type-2 Polymer Standard Solution | 81.51 | 25.5 |
| Deionized water | 0 | 0.0 |
| Total | 319.72 | 100 |
| Amount of fragrance in isolated composition | | 8.1 |

Example 74

| Water Immiscible Fluid phase | Amount, gm | % by weight |
|---|---|---|
| Dimethicone 200, 10000 cSt, Dow Corning | 51.106 | 43.7 |
| Dispersant Rewoquat SQ1, Evonik | 2.5 | 2.1 |

-continued

| Water Immiscible Fluid phase | Amount, gm | % by weight |
|---|---|---|
| Example 55 | 51.106 | 43.7 |
| Organo 34 organoclay, AMCOL Intl. | 10.212 | 8.7 |
| Propylene Carbonate | 2.047 | 1.7 |
| Total | 116.971 | 100 |

| Deposition-Aid treated fragrance composition | Amount, gm | % by weight |
|---|---|---|
| Water Immiscible Fluid phase | 113.84 | 35.1 |
| Mixed Polymer Standard Solution | 125 | 38.5 |
| Deionized water | 0 | 0.0 |
| Type-2 Polymer Standard Solution | 85.38 | 26.3 |
| Deionized water | 0 | 0.0 |
| Total | 324.22 | 100 |
| Amount of fragrance in isolated composition | | 5.96 |

Washing and Drying Procedure:

All washing procedures were conducted using 42.87 g of ALL Free and Clear (available from SUN PRODUCTS Corp.) a medium load wash cycle. A warm wash and one cold rinse were used in a Kenmore top loader. Approximately, 16 100% cotton Martex Brand Commercial Pack hand towels (obtained at Costco stores in the USA) for a towel weight of 2.5 Kg were washed. No commercially-sold fabric softeners were added. The fragrance wash samples were added separately to the wash water as it fills the tank, after adding the detergent.

At approximately five minutes into the washing cycle and after the agitation of the laundry load has started, the pH (pH paper) and the temperature of the wash water was recorded. Additionally, a 2 oz. sample of the wash water is removed ("wash dilution sample"). At approximately two minutes into the agitation of the rinse cycle water (approximately 9 minutes into the entire rinse cycle), the pH and the temperature of the rinse water was recorded. At the same time, a 2 oz. sample of the rinse water is taken for testing ("rinse dilution sample").

General Parameters for the Wash Cycle:

| Water Volume Used: Cold Water: | 12.21 gallons |
|---|---|
| Hot Water: | 3.88 gallons |
| Total Volume (wash): | 16.09 gallons |
| For the rinse cycle (cold) at the above mentioned settings; | |
| Water Volume Used: Cold Water: | 15.33 gallons |
| Total Volume (rinse): | 15.33 gallons |

Wet towels, wash dilution samples, and rinse dilution samples are evaluated for fragrance intensity. Wet towels were either line dried or machine dried. Line drying was conducted for 24 hours in ambient atmosphere (approximately 20-25° C. and approximately 30% to 70% humidity). Machine drying was conducted with a Kenmore 6.7 cu. ft. Super Capacity HE2 Electric Dryer (available from SEARS BRANDS, LLC) at "normal" setting and medium temperature (30° C. to start increasing to 69° C.) for 40 min. The humidity during the machine drying varied from about 42% at the start of the drying cycle to about 8%. Line dried and tumble dried towels were used fragrance intensity & longevity evaluations. Individual towel evaluations were conducted over two week periods. Evaluations included both paired testing (a forced ranking between pairs of towels) and intensity ranking (scale 1-6).

The foregoing description is given for clearness of understanding only, and no unnecessary limitations should be understood therefrom, as modifications within the scope of the invention may be apparent to those having ordinary skill in the art.

What is claimed is:

1. A method of enhancing adherence of a fragrance composition to a substrate, comprising:
   coating the fragrance composition with a polymer selected from the group consisting of a Type-1 Polymer, a Type-2 Polymer, and a mixture thereof, to form an adherent fragrance composition, and;
   contacting the substrate with the adherent fragrance composition;
   wherein the fragrance composition comprises a fragrance particulate and a viscoelastic gel, and the fragrance particulate comprises a fragrance and is coated with the viscoelastic gel,
   wherein the viscoelastic gel comprises κ-carrageenan,
   wherein the Type-1 Polymer has a cationic nitrogen content of at least about 3 wt. % and a weight average molecular weight of less than about 800,000 Dalton, and is selected from the group consisting of poly(diallyldimethyl ammonium halide), poly(DADMAC), and combinations thereof, and
   wherein the Type-2 Polymer has a cationic nitrogen content of less than about 3 wt. % and a weight average molecular weight of greater than about 1,000,000 Dalton, and is selected from the consisting of a cationic guar gum, a cationic cellulose, a cationic starch, hydrophobically-modified versions thereof, and combinations thereof.

2. The method of claim 1, wherein the substrate is selected from the group consisting of teeth, hair, skin, fabric, plastic, polymer, glass, stone, metal, insects, plants, fungus, yeast, foods, and mixtures thereof.

3. The method of claim 2, wherein the composition contacts the fabric with water during washing of the fabric.

4. A fragrant substrate comprising:
   a substrate;
   an adherent fragrance composition disposed on the substrate, the adherent fragrance composition comprising:
   a fragrance composition comprising a fragrance particulate and a viscoelastic gel, wherein the fragrance particulate comprises a fragrance and is coated with the viscoelastic gel, and the viscoelastic gel comprises κ-carrageenan; and
   a polymer coating the fragrance composition, the polymer being selected from the group consisting of a Type-1 Polymer, a Type-2 Polymer, and a mixture thereof, wherein:
   the Type-1 Polymer has a cationic nitrogen content of at least about 3 wt. % and a weight average molecular weight of less than about 800,000 Dalton, and is selected from the group consisting of poly(diallyldimethyl ammonium halide), poly(DADMAC), and combinations thereof, and
   the Type-2 Polymer has a cationic nitrogen content of less than about 3 wt. % and a weight average molecular weight of greater than about 1,000,000 Dalton, and is selected from the consisting of a cationic guar gum, a cationic cellulose, a cationic starch, hydrophobically-modified versions thereof, and combinations thereof.

5. The fragrant substrate of claim 4, wherein the substrate is selected from the group consisting of hair, skin, fabric, plastic, polymer, glass, stone, metal, insects, plants, fungus, yeast, and mixtures thereof.

6. The fragrant substrate of claim 5, wherein the substrate is a fabric.

* * * * *